(12) United States Patent
Lineaweaver et al.

(10) Patent No.: US 11,596,793 B2
(45) Date of Patent: Mar. 7, 2023

(54) SHIFTING OF OUTPUT IN A SENSE PROSTHESIS

(71) Applicants: Sean Lineaweaver, Gig Harbor, WA (US); John Michael Heasman, East Melbourne (AU)

(72) Inventors: Sean Lineaweaver, Gig Harbor, WA (US); John Michael Heasman, East Melbourne (AU)

(73) Assignee: Cochlear Limited, Macquarie University (AU)

( * ) Notice: Subject to any disclaimer, the term of this patent is extended or adjusted under 35 U.S.C. 154(b) by 39 days.

(21) Appl. No.: 16/840,890

(22) Filed: Apr. 6, 2020

(65) Prior Publication Data
US 2020/0330762 A1     Oct. 22, 2020

Related U.S. Application Data

(60) Continuation of application No. 15/948,431, filed on Apr. 9, 2018, now Pat. No. 10,610,687, which is a division of application No. 15/157,968, filed on May 18, 2016, now Pat. No. 9,937,346.

(60) Provisional application No. 62/327,648, filed on Apr. 26, 2016.

(51) Int. Cl.
*A61N 1/36*      (2006.01)
*A61N 1/05*      (2006.01)

(52) U.S. Cl.
CPC ...... *A61N 1/36036* (2017.08); *A61N 1/36038* (2017.08); *A61N 1/36046* (2013.01); *A61N 1/0543* (2013.01)

(58) Field of Classification Search
None
See application file for complete search history.

(56) References Cited

U.S. PATENT DOCUMENTS

| | | | | |
|---|---|---|---|---|
| 6,330,339 B1 * | 12/2001 | Ishige | ........... | H04R 25/502 381/312 |
| 9,313,585 B2 * | 4/2016 | Lunner | ........... | H04R 25/558 |
| 2007/0286350 A1 * | 12/2007 | Krause | ........... | H04M 3/42391 379/22.02 |
| 2009/0187065 A1 * | 7/2009 | Basinger | ........... | A61N 1/36038 600/25 |
| 2014/0107493 A1 * | 4/2014 | Yuen | ........... | A61B 5/6898 600/473 |
| 2014/0369537 A1 * | 12/2014 | Pontoppidan | ........... | G06V 40/19 381/314 |
| 2016/0144178 A1 * | 5/2016 | Hillbratt | ........... | A61N 1/36036 607/57 |
| 2016/0302013 A1 * | 10/2016 | Andersson | ........... | H04R 25/70 |

* cited by examiner

*Primary Examiner* — Brian T Gedeon
(74) *Attorney, Agent, or Firm* — Pilloff Passino & Cosenza LLP; Martin J. Cosenza

(57) ABSTRACT

A method, including the action of operating a sense prosthesis, such as a retinal implant, according to a first operating regime while the recipient has a first fatigue level, and operating the sense prosthesis according to a second operating regime while the recipient has a second fatigue level that is greater than the first fatigue level.

30 Claims, 18 Drawing Sheets

SHIFTING OF OUTPUT IN A SENSE PROSTHESIS

CROSS-REFERENCE TO RELATED APPLICATIONS

This application is a Continuation application of U.S. patent application Ser. No. 15/948,431, filed Apr. 9, 2018, which is a Divisional application of U.S. patent application Ser. No. 15/157,968, filed May 18, 2016 (now U.S. Pat. No. 9,937,346), which claims priority to Provisional U.S. Patent Application No. 62/327,648, entitled DOWNSHIFTING OF OUTPUT IN A SENSE PROSTHESIS, filed on Apr. 26, 2016, naming Sean LINEAWEAVER of Gig Harbor, Wash. as an inventor, the entire contents of each application being incorporated herein by reference.

BACKGROUND

People suffer from sensory loss, such as, for example, eyesight loss. Such people can often be totally blind or otherwise legally blind. So called retinal implants can provide stimulation to a recipient to evoke a sight percept. In some instances, the retinal implant is meant to partially restore useful vision to people who have lost their vision due to degenerative eye conditions such as retinitis pigmentosa (RP) or macular degeneration.

Typically, there are three types of retinal implants that can be used to restore partial sight: epiretinal Implants (on the retina), subretinal Implants (behind the retina), and suprachoroidal implants (above the vascular choroid). Retinal implants provide the recipient with low resolution images by electrically stimulating surviving retinal cells. Such images may be sufficient for restoring specific visual abilities, such as light perception and object recognition.

Still further, other types of sensory loss entail somatosensory and chemosensory deficiencies. There can thus be somatosensory implants and chemosensory implants that can be used to restore partial sense of touch or partial sense of smell and/or taste.

Another type of sensory loss is hearing loss, which may be due to many different causes, generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses, commonly referred to as cochlear implants, convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. One type of medical device where there is utilitarian value in making such adjustments is the above-noted cochlear implant. That said, other types of medical devices, such as other types of hearing prostheses, and other types of prosthesis, such as a retinal implant, exist where there is utilitarian value in fitting such to the recipient.

BRIEF DESCRIPTION OF THE DRAWINGS

Embodiments are described below with reference to the attached drawings, in which.

DETAILED DESCRIPTION

At least some of the teachings detailed herein can be implemented in retinal implants. Accordingly, any teaching herein with respect to an implanted prosthesis corresponds to a disclosure of utilizing those teachings in/with a retinal implant, unless otherwise specified. Still further, at least some teachings detailed herein can be implemented in somatosensory implants and/or chemosensory implants. Accordingly, any teaching herein with respect to an implanted prosthesis can correspond to a disclosure of utilizing those teachings with/in a somatosensory implant and/or a chemosensory implant. That said, exemplary embodiments can be directed towards hearing prostheses, such as cochlear implants. The teachings detailed herein will be described for the most part with respect to cochlear implants or other hearing prostheses. However, in keeping with the above, it is noted that any disclosure herein with respect to a hearing prosthesis corresponds to a disclosure of utilizing the associated teachings with respect to any of the other prostheses detailed herein or other prostheses for that matter.

Figure 1:
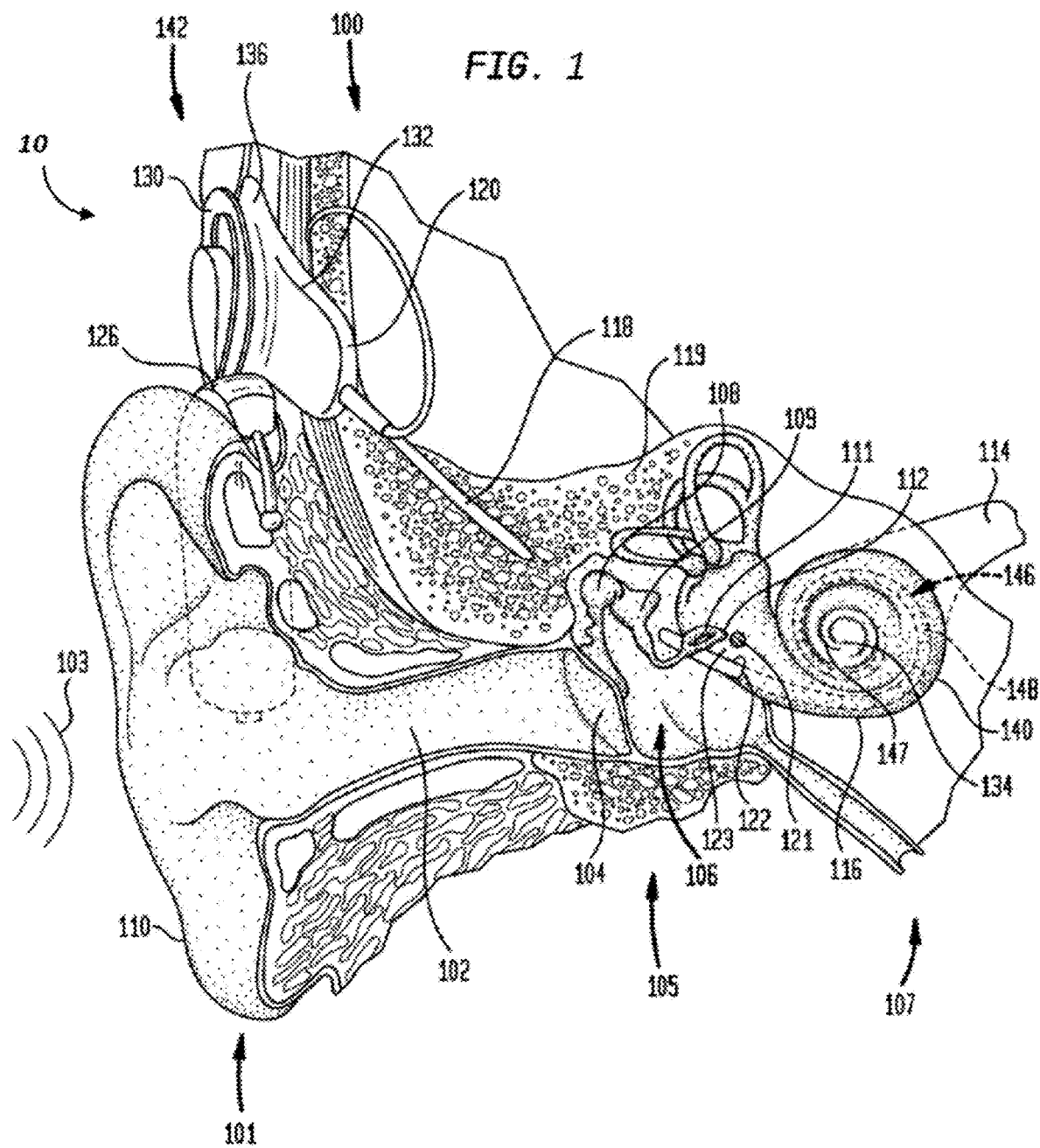
FIG. 1 is a perspective view of an exemplary hearing prosthesis in which at least some of the teachings detailed herein are applicable.

FIG. 1 is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.). Additionally, it is noted that the teachings detailed herein are also applicable to fitting and/or using other types of hearing prostheses, such as by way of example only and not by way of limitation, bone conduction devices, direct acoustic cochlear stimulators, middle ear implants, etc. Indeed, it is noted that the teachings detailed herein are also applicable to so-called hybrid devices. In an exemplary embodiment, these hybrid devices apply both electrical stimulation and acoustic stimulation to the recipient. Any type of hearing prosthesis to which the teachings detailed herein and/or variations thereof can have utility can be used in some embodiments of the teachings detailed herein.

The recipient has an outer ear 101, a middle ear 105 and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery that is recharged by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive, and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 2:
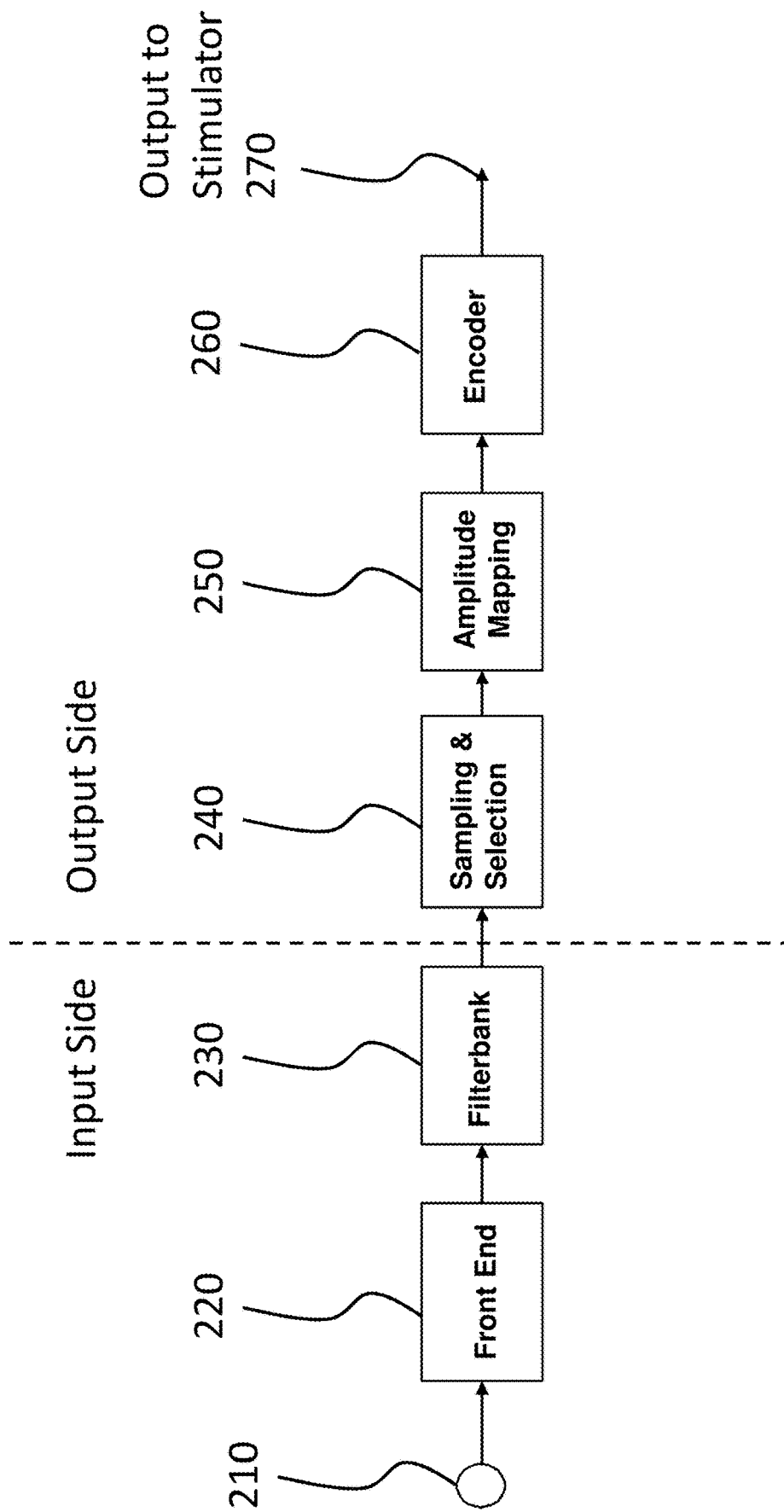
FIG. 2 presents an exemplary functional schematic according to an exemplary embodiment.

FIG. 2 presents an exemplary high level functional schematic of an exemplary embodiment, with emphasis on an overall signal processing scheme utilized in at least some embodiments. As can be seen, a stimulus capture device 210, which can correspond to an image sensor, such as a digital image sensor (e.g., CCD, CMOS), or a sound sensor, such as a microphone, etc. The transducer of device 210 outputs a signal to the components of the so-called front end 220, which amplifies and combines the signals from device 210, and, in some embodiments, can incorporate automatic gain control (AGC). In an exemplary embodiment, component of the front-end can include amplifiers, and/or prefilters, etc.

Output from the front end 220 is provided to a filterbank 230, which splits the light or sound, depending on the embodiment, into multiple frequency bands. With respect to embodiments directed towards hearing prostheses, the splitting emulates the behavior of the cochlea in a normal ear, where different locations along the length of the cochlea are sensitive to different frequencies. In at least some exemplary embodiments, the envelope of each filter output controls the amplitude of the stimulation pulses delivered to a corresponding electrode. With respect to hearing prostheses, electrodes positioned at the basal end of the cochlea (closer to the middle ear) are driven by the high frequency bands, and electrodes at the apical end are driven by low frequencies. In at least some exemplary embodiments, the outputs of filter bank 230 are a set of signal amplitudes per channel or plurality of channels, where the channels are respectively divided into corresponding frequency bands.

As can be seen in FIG. 2, the functional schematic has been divided into an input side and an output side. Accordingly, various references will be made to "input stages" and "output stages." As used herein, input stages have at least the following functionalities: management of the input, such as the utilization of feedback elimination algorithms where a portion of the signal coming from capture device 210 is canceled and data signal cancellation, where again, a portion of the signal from capture device 210 is canceled. In an exemplary embodiment, the aforementioned canceling can be utilized to achieve noise reduction, and therefore, such cancellation that occurs on the input side corresponds to an input stage operation. Speech enhancement and beamforming/directional sound capture techniques are also input side processes. Of course, as noted above, the prefiltering and the filtering of filter bank 230 also entail the management of the input. The utilization of signal/data compression, etc. so as to enable the sampling and selection block 240 to perform in a more efficient manner and/or in a power conservancy mode is also included in the input side signal management.

The sampling and selection block 240 (on the output side) samples the output of the filter bank 230, such as the filterbank envelopes, and determines the timing and pattern of the stimulation on each electrode. In general terms, sampling and selection block 240 selects certain channels as a basis for stimulation, based on the amplitude and/or other factors. Still in general terms, sampling and selection block 240 determines how stimulation will be based on the channels corresponding to the divisions established by the filter bank 230. In at least some exemplary embodiments, the actions of the sampling and selection block are executed by a so-called sound processor with respect to a hearing prosthesis.

In some exemplary embodiments, stimulation rates on each electrode (electrodes of a cochlear electrode array, for example) can range from 250 to 3500 pulses per second, and embodiments include stimulation rates at any value or range of values therebetween in 1 pulse per second increments (e.g., 350 pulses per second, 3333 pulses per second, 355 to 941 pulses per second, etc.). In some other exemplary embodiments, stimulation rates on each electrode (electrodes of a retinal electrode assembly for example) may range from 50 pulses to 2,500 pulses per second, and embodiments include stimulation rates at any value or range of values therebetween in 1 pulse per second increments. In an exemplary embodiment, the stimulation is applied in pulses having pulse widths of 10 to 25 µs duration or any value or range of values therebetween in one microsecond increments. The amplitude mapping block 250 compresses the filterbank envelopes to determine the current level of each pulse. Currents having utilitarian value can be in the range 100 to 1000 µA, or any value or range of values therebetween in 1 µA increments. Such current levels vary both amongst implant recipients and across the electrode apparatus. With respect to a hearing prosthesis, amplitude and mapping block 250 is set by a clinician, or more accurately, the algorithm that is utilized to set the current levels is set by the clinician, and the sound processor, using that algorithm, implements the amplitude of the stimulation based on that algorithm. The final block (final by way of example) is the encoder 260, which encodes the data provided from block 250, so that the data can be transmitted to the stimulator. In an exemplary embodiment, the data is encoded for the purposes of transmission over a 5 MHz inductance link via a transcutaneous transmission to an implanted stimulator, and outputted (as represented by arrow 270) to the stimulator component that stimulates the tissue of the recipient to evoke the vision and/or hearing percept.

Figure 3:
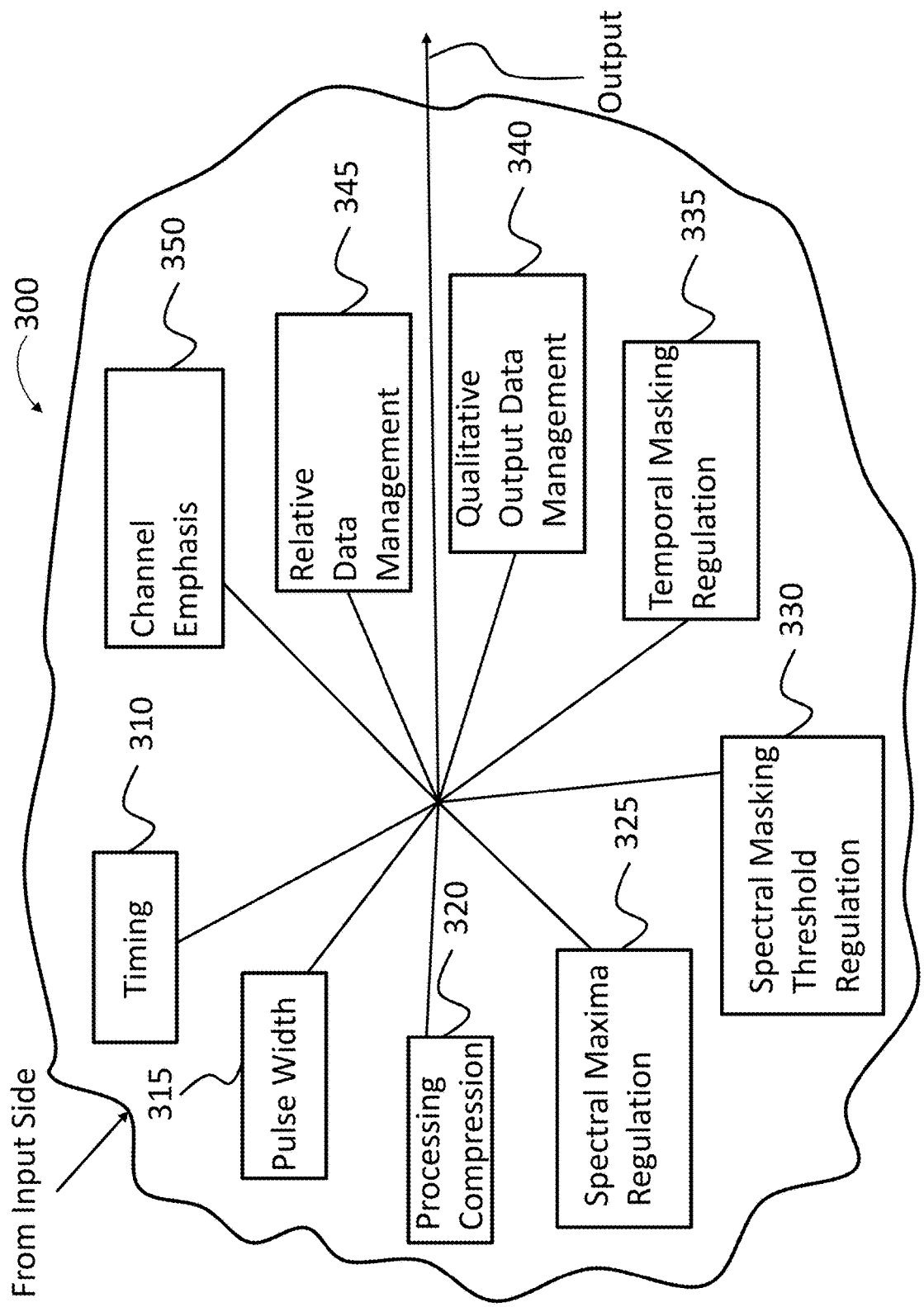
FIG. 3 presents another exemplary functional schematic according to another exemplary embodiment.

The functional diagram of FIG. 2 presents the various blocks in a linear fashion. It is noted however, that in at least some exemplary embodiments, this is done in a nonlinear fashion as well. Note further that the output side functionalities can have various subfunctions that can be implemented and/or not implemented, depending on how the prosthesis is utilized. In this regard, FIG. 3 depicts an exemplary functional schematic of an operation of at least a portion of the output side stages as a conceptual amalgamation where input from the input side enters the output side processing 300, which includes various blocks as will now be detailed, which results in output 390 that is utilized to evoke a sensory percept, such as a hearing percept in this exemplary embodiment.

More specifically, as can be seen, the output side processing 300 includes a timing block 310. Timing block 310 is utilized to determine the stimulation rate(s) that will be applied to the tissue stimulator, at least with respect to electrical stimulation. By way of example only and not by way of limitation, an electrode of a retinal implant may be stimulated at a rate of 1000 pulses per second, whereas in at least some exemplary embodiments, there may be utilitarian value to instead stimulate at a rate of 500 pulses per second. Still further by way of example, with respect to a cochlear implant, an exemplary stimulation rate of given electrode that is being utilized to evoke a hearing percept is at about 900 pulses per second, whereas in some alternate embodiments, there can be utilitarian value with respect to stimulating at a rate of 500 pulses per second, a slower rate. In an exemplary embodiment, stimulation can occur for a given electrode from about 5000, 4750, 4500, 4250, 4000, 3750, 3500, 3250, 3000, 2750, 2500, 2250, 2000, 1900, 1800, 1700, 1600, 1500, 1450, 1400, 1350, 1300, 1250, 1200, 1150, 1100, 1050, 1000, 950, 900, 850, 800, 750, 700, 650, 600, 550, 500, 450, 400, 350, 300, 250, 200, 150, 100 or 50 or any value or range of values therebetween in 1 pulse per second increments. To be clear, these data points/ranges are but exemplary (as is the case with respect to all of the data points detailed herein unless otherwise specified). In some embodiments, stimulation can occur for a given electrode at ranges above these values or below these values. As will be disclosed herein, an exemplary embodiment entails operating a sense prosthesis during a first temporal period where the stimulation rate occurs at about 900 pulses per second, and then, due to a scenario that will be described in greater detail below, operating the hearing prosthesis such that the stimulation rate occurs at about 500 pulses per second. Still further, in an exemplary embodiment, there can be a scenario where the hearing prosthesis is operated such that the stimulation rate that occurs is about 700 pulses per second.

Figure 4:
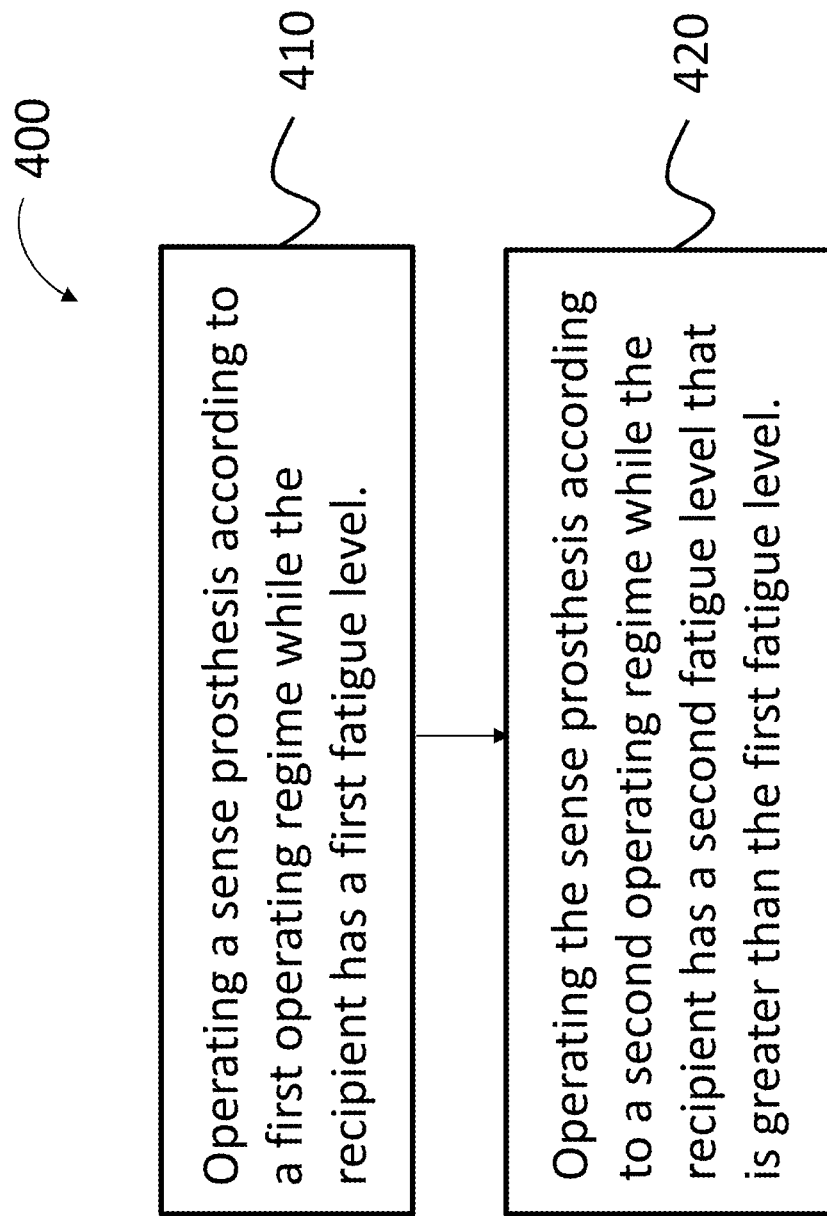
FIG. 4 resents an exemplary flowchart for an exemplary method according to an exemplary embodiment.

More specifically, now with reference to FIG. 4, there is an exemplary algorithm presented for an exemplary embodiment representing method 400. Method 400 includes method action 410, which entails operating a sense prosthesis according to a first operating regime while the recipient has a first fatigue level. In an exemplary embodiment, the recipient is fatigued relative to that which is the case at a prior temporal period, as will be described below. In an exemplary embodiment, the sense prosthesis is operated such that the stimulation rate of an electrode thereof is more than 600 pulses per second and less than 800 pulses per second. In an exemplary embodiment, the hearing prosthesis is operated such that the electrode is stimulated at 700 pulses per second. In an exemplary embodiment, the sense prosthesis is operated such that the stimulation rate of an electrode is anywhere between 400 pulses per second and 3000 pulses per second or any value or range of values therebetween in one pulse per second increments. This can be considered a first scenario of use, with a recipient is fatigued, such as, by way of example, mentally fatigued. In an exemplary embodiment, "fatigued" entails a physiological state where the recipient effectively does not perform at a given task as well as he or she otherwise would have in a non-fatigued state. Some additional details of this will be described in greater detail below.

Method 400 further includes method action 420, which entails operating the sense prosthesis according to a second operating regime while the recipient has a second fatigue level that is greater than the first fatigue level. Here, the recipient is more fatigued than that which was the case during operation of the hearing prosthesis at the first operating regime. By "more fatigued," it is meant that the recipient has a physiological state that results in the recipient effectively not performing a given task as well as he or she otherwise would have at the first fatigue level. Again, both fatigue levels are differentiated from a physiological state where there is no fatigue (a zero fatigue level). In an exemplary embodiment, the sense prosthesis is operated according to the second operating regime such that the stimulation rate of an electrode thereof is less than 600 pulses per second. In an exemplary embodiment, the hearing prosthesis is operated such that the electrode is stimulated at 500 pulses per second. In an exemplary embodiment, the sense prosthesis is operated such that the stimulation rate of an electrode is anywhere between 100 pulses per second and 1500 pulses per second or any value or range of values therebetween in one pulse per second increments. This can be considered a second scenario of use.

Figure 5:
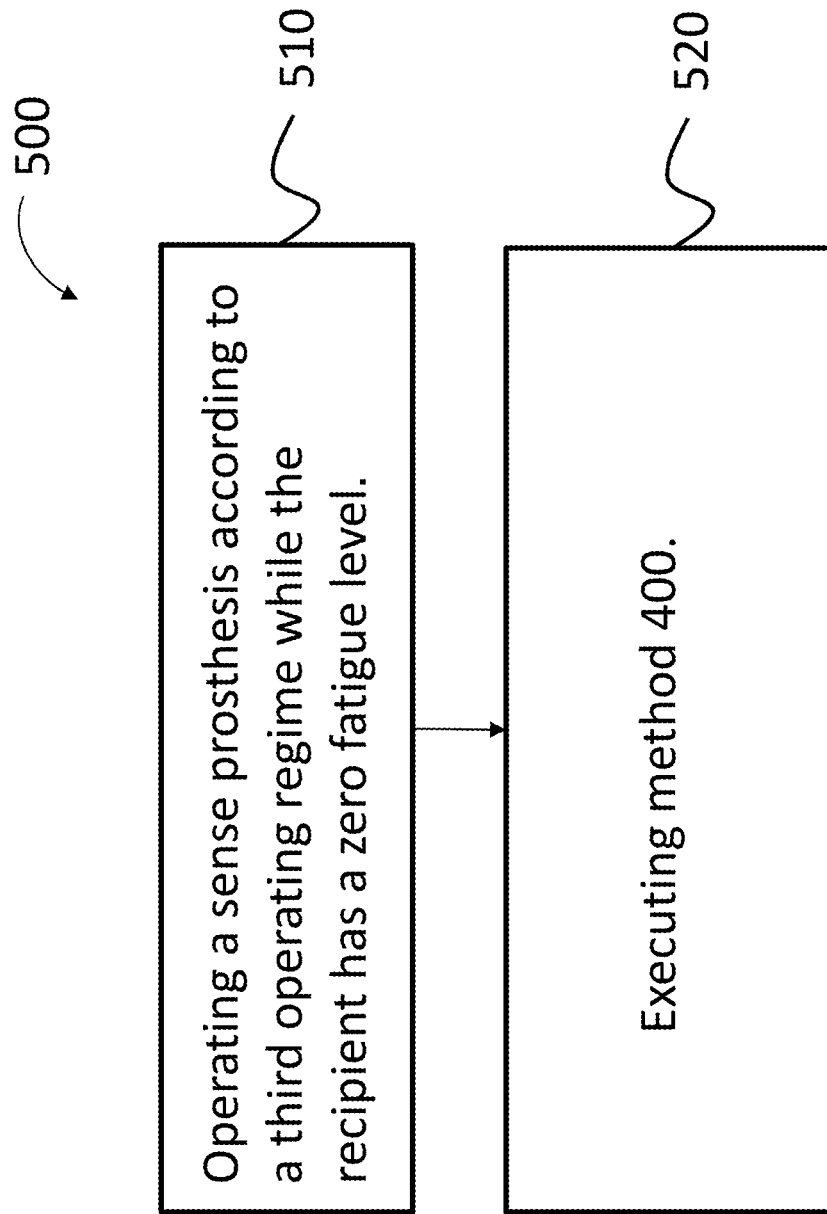
FIG. 5 presents another exemplary flowchart for an exemplary method according to an exemplary embodiment.

FIG. 5 depicts another exemplary algorithm for an exemplary embodiment. FIG. 5 represents method 500. Method 500 includes method action 510, which entails operating a sense prosthesis according to a third operating regime while the recipient has a zero fatigue level. In an exemplary embodiment, this can entail operating the sense prosthesis at the beginning of one's workday or at the beginning of one's school day, where the recipient is not fatigued (this as opposed to tired, or a scenario where the recipient worked late into the night or studied late into the night, where the recipient begins the workday and/or school day in a fatigued state). Here, a zero fatigue level is a physiological state where the recipient is, all things being equal, most capable to perform a given task at hand relative to any other state in which the recipient might be, if only as a matter of statistics (i.e., the recipient has a general ability to perform a given task in an un-fatigued state, and these general abilities decline as the level of fatigue increases—it might be that even in a non-fatigued state, the recipient does not perform such tasks relatively well as compared to a statistically significant group—in this regard, the ability to perform is subjective and relative to only the recipient).

In an exemplary embodiment, the third operating regime is an operating regime such that the stimulation rate of an electrode of the sense prosthesis is more than 800 pulses per second. In an exemplary embodiment, the hearing prosthesis is operated such that the electrode is stimulated at 900 pulses per second. In an exemplary embodiment, the sense prosthesis is operated such that the stimulation rate of an electrode is anywhere between 600 pulses per second and 5000 pulses per second, or any value or range of values therebetween in one pulse per second increments.

Figure 6:
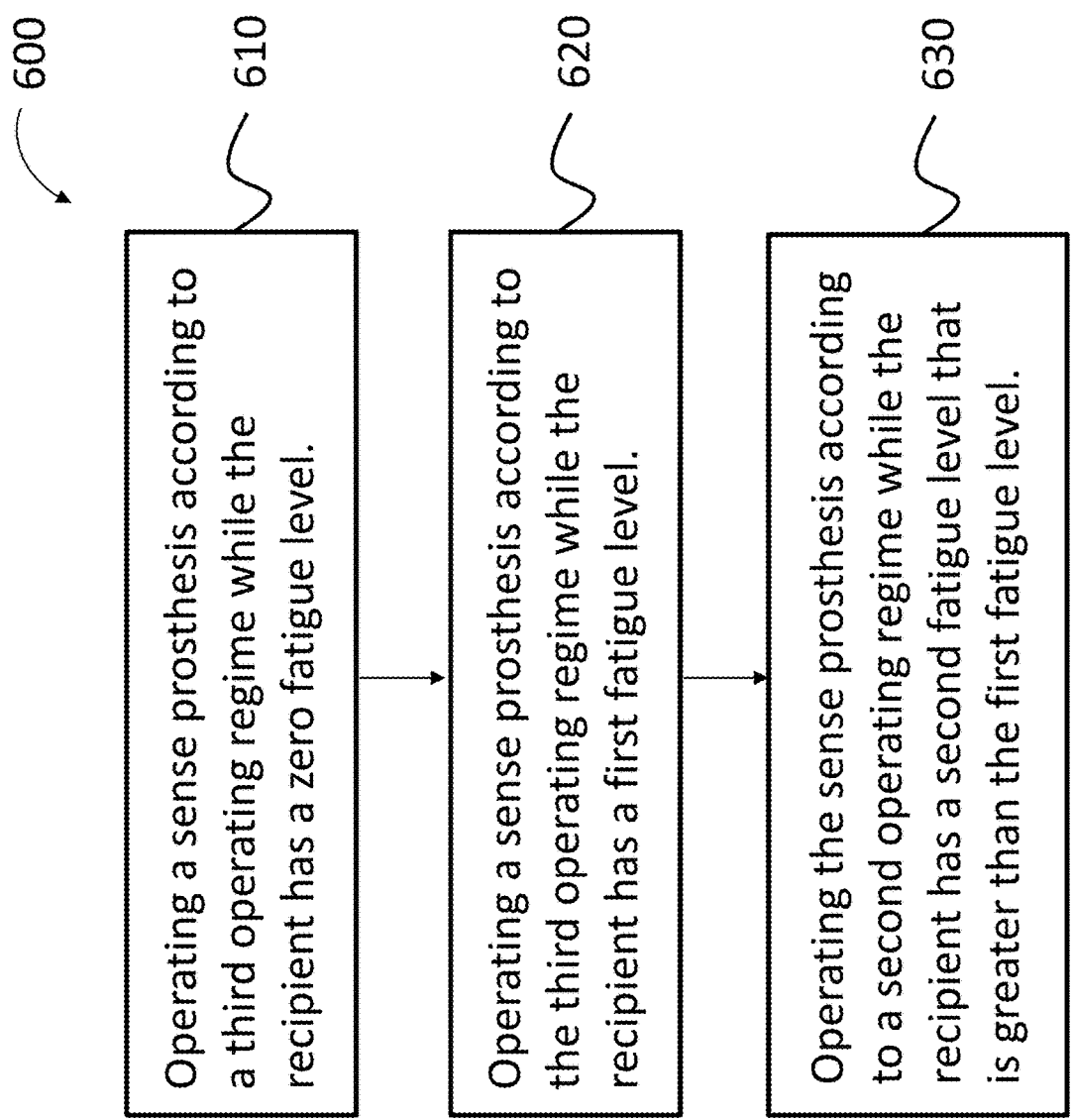
FIG. 6 presents another exemplary flowchart for an exemplary method according to an exemplary embodiment.

FIG. 6 presents another alternate algorithm for an exemplary embodiment. In FIG. 6, there is presented a flowchart for a method 600. As can be seen, method 600 includes method action 610, which entails operating a sense prosthesis according to a third operating regime while the recipient has a zero fatigue level. With respect to the stimulation rates of the electrodes, in an exemplary embodiment, this could be a stimulation rate of about 800, 900, or 1000 pulses per second. In an exemplary embodiment, this corresponds to the stimulation rate of above 400 pulses per second or any value thereabove in one pulse per second increments.

Method 600 further includes method action 620, which entails operating the sense prosthesis according to the third operating regime while the recipient has a first fatigue level. Here, the first fatigue level corresponds to that detailed above—something that is effectively in between a zero fatigue level, and a greater fatigue level, where the levels noticeably impact the recipient's ability to perform given tasks (e.g., such as listening/comprehending that to which he or she is listening). However, the stimulation rate is not changed from that which was the case while the recipient was at the zero fatigue level. (As will be detailed below, in some exemplary embodiments, other features of the hearing prosthesis are utilized in a different manner while the recipient is at the first fatigue level other than the stimulation rate.) That is, here, the stimulation rates are unchanged, even though the recipient is more fatigued than that which was the case during method action 610. As can be seen, this method differentiates from the method of FIG. 5 in that, with respect to the method of FIG. 6, while the recipient is at the first fatigue level, the stimulation rate used is the same as that which was used during the zero fatigue level whereas in the method of FIG. 5, the stimulation rate was reduced when the recipient was at the first fatigue level relative to that which was the case while the recipient was at the zero fatigue level. As will be understood, in these methods, reference to the first, second, and third operating regimes corresponds to reference for naming purposes only. Here, there is no first operating regime—only a second and third operating regime. Again, these are merely names for accounting purposes.

Method 600 further includes method action 630, which entails operating the sense prosthesis according to a second operating regime while the recipient has a second fatigue level that is greater than the first fatigue level. In an exemplary embodiment, with respect to the stimulation rates of the electrodes, this could be a stimulation rate of about 300, 400, 500, 600, or 700 pulses per second. In an exemplary embodiment, this corresponds to a stimulation rate of below 1500 pulses per second or any value or range of values therebetween in one pulse per second increments.

Figure 7:
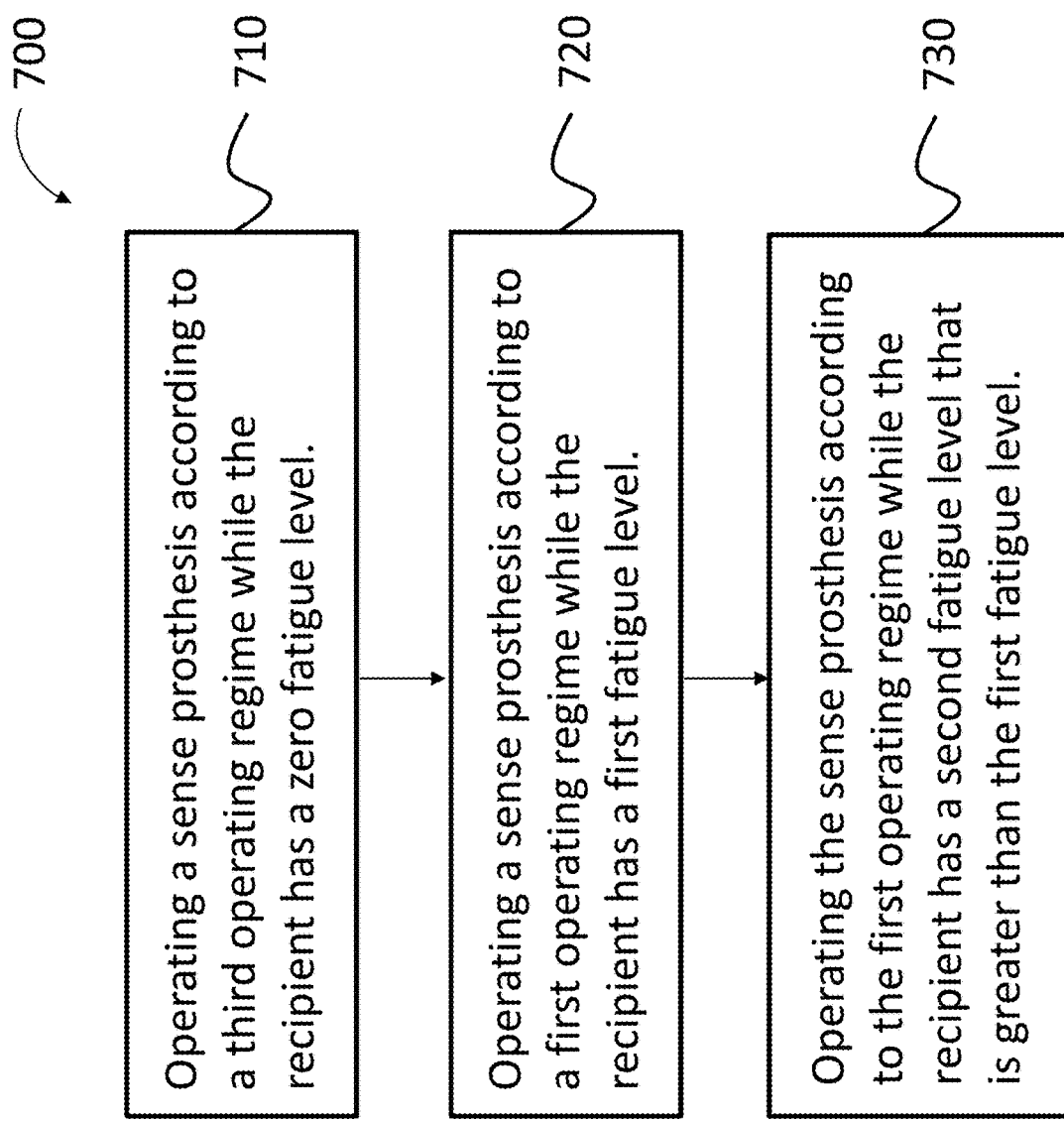
FIG. 7 presents another exemplary flowchart for an exemplary method according to an exemplary embodiment.

FIG. 7 presents another alternate algorithm for an exemplary embodiment. In FIG. 7, there is presented a flowchart for a method 700. As can be seen, method 700 includes method action 710, which entails operating a sense prosthesis according to a third operating regime while the recipient has a zero fatigue level. With respect to the stimulation rates of the electrodes, in an exemplary embodiment, this could be a stimulation rate of about 800, 900, or 1000 pulses per second. In an exemplary embodiment, this corresponds to the stimulation rate of above 400 pulses per second or any value thereabove in one pulse per second increments.

Method 700 further includes method action 720, which entails operating the sense prosthesis according to a first operating regime while the recipient has a first fatigue level. Here, the first fatigue level corresponds to that detailed above—something that is effectively in between a zero fatigue level, and a greater fatigue level, where the levels noticeably impact the recipient's ability to perform given tasks (e.g., such as listening/comprehending that to which he or she is listening). In an exemplary embodiment, with respect to the stimulation rates of the electrodes, this could be a stimulation rate of about 300, 400, 500, 600, or 700 pulses per second. In an exemplary embodiment, this corresponds to a stimulation rate of below 1500 pulses per second or any value or range of values therebetween in one pulse per second increments.

Method 600 further includes method action 730, which entails operating the sense prosthesis according to the first operating regime while the recipient has a second fatigue level that is greater than the first fatigue level. Here, the stimulation rates are unchanged, even though the recipient is more fatigued than that which was the case during method action 720. As can be seen, this method differentiates from the method of FIG. 5 in that in the method of FIG. 7, while the recipient is at the second fatigue level, the stimulation rate used is the same as that which was used during the first fatigue level whereas in the method of FIG. 5, the stimulation rate was reduced when the recipient was at the second fatigue level relative to that which was the case while the recipient was at the first fatigue level. Corollary to the embodiment detailed above with respect to FIG. 6, in some other embodiments, other features of the hearing prosthesis are changed so as to account for the second fatigue level other than adjusting the stimulation rate.

Corollary to the above, in an exemplary embodiment, the prosthesis can be operated according to an operation regime in which the prosthesis limits a resulting stimulation rate of a tissue stimulator that stimulates tissue to evoke a hearing and/or a vision percept relative to that which is the case in another operating regime.

Still with reference to FIG. 3, output side processing 300 includes a pulse width block 315. Pulse width block 315 determines the pulse widths of the stimulation signals applied to the electrodes. In an exemplary embodiment, the pulse width can be from about 75 µs, 70 µs, 65 µs, 60 µs, 55 µs, 50 µs, 45 µs, 40 µs, 35 µs, 30 µs, 25 µs, 20 µs, 15 µs, 10 µs, 5 µs, or any value or range of value therebetween in 1 µs increments. As with the timing block 310, the hearing prosthesis can be operated depending on a range of scenarios to have different pulse widths as will be detailed herein by way of example only and not by way of limitation.

In view of this feature of the exemplary sense prosthesis, it is noted that in an exemplary embodiment, with respect to FIGS. 5-7 (the methods thereof), the third operating regime corresponds to the smallest pulse width relative to the first and second operating regimes. The first operating regime can correspond to an operating regime where the pulse width is larger than that of the third operating regime. Still further, the second operating regime can correspond to an operating regime where the pulse width is larger than that of the third operating regime and the first operating regime.

Still further, output side processing 300 includes compression block 320. In an exemplary embodiment, the prosthesis utilizes a signal processing strategy that is consistent for most of its utilization time. That is, this can be considered to be a default speech processing strategy. With respect to a hearing prosthesis, such can be the ACE processing strategy, or some other processing strategy that does not utilize perceptual coding concepts. That said, in some exemplary scenarios, there can be utilitarian value with respect to utilizing a different processing strategy or otherwise implementing a modification of the given processing strategy. In an exemplary embodiment, such entails utilizing a processing strategy that utilizes psychophysical processing strategies that utilize perceptual coding concepts that can, for example, take into account the fact that some environmental inputs (sound, light, etc.) are perceptually masked by other inputs (sound, light—this is sometimes referred to in the art as a masking phenomenon), and therefore need not be presented as stimulation components (audio, visual component, depending on the embodiment). Masking functionally can result in fewer spectral components (or maxima) that are ultimately coded. In at least some exemplary embodiments of the embodiments detailed herein, the prosthesis changes from a non-psychophysical processing strategy to a psychophysical processing strategy upon the occurrence of a different scenario, again which will be detailed below. In an exemplary embodiment with respect to a hearing prosthesis, the psychophysical sound processing strategies used in at least some of these exemplary embodiments utilize masking models to estimate effects of the masking phenomena on a recipient, and in turn, to process and encode received sound information into corresponding encoded electronic signals that may omit sounds that would be perceptually masked. A similar concept can be utilized with respect to light for a retinal prosthesis.

Figure 8:
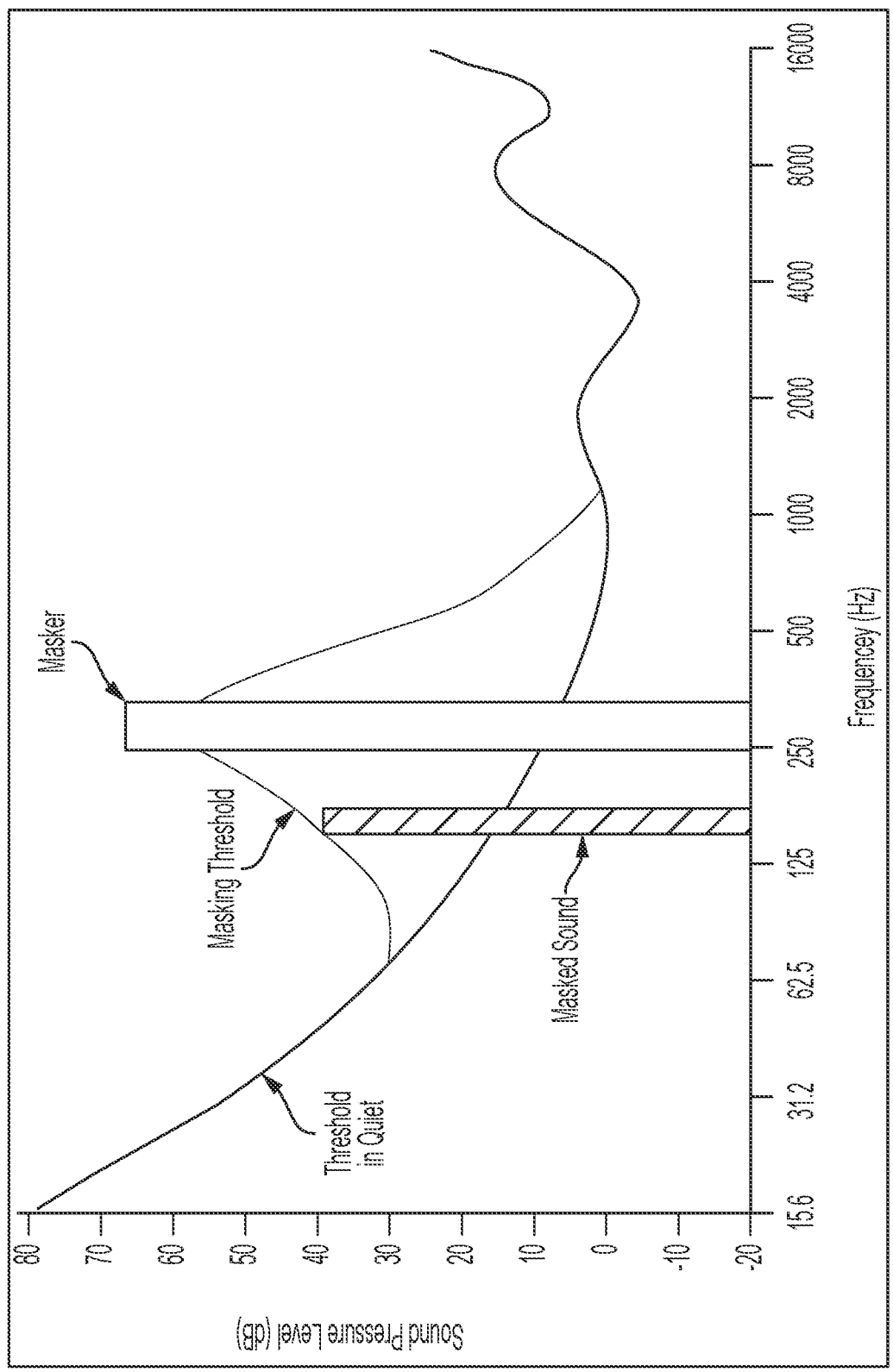
FIG. 8 presents an exemplary illustration of an exemplary phenomenon associated with an exemplary embodiment.

Accordingly, in an exemplary embodiment, there is a psychophysical processing strategy, such as a sound processing strategy, can depend in part on sound intensity parameters. FIG. 8 illustrates an example of an implementation of a masking model to achieve perceptual coding, wherein a masker or masking sound (e.g., a nearby car horn) makes it difficult for a person to hear a masked sound (e.g., words that are whispered to the person). In this example, the louder sound masks the softer sound. Accordingly, in an exemplary embodiment, there is utilitarian value with respect to eliminating the content of the masked sound from the output, at least in some exemplary scenarios. Alternatively or in addition to this, in an exemplary embodiment, there is utilitarian value with respect to eliminating the content of the masking sound from the output, at least in some exemplary scenarios. While this example has been directed towards sound frequencies, in an exemplary embodiment, the same theory/principle of operation is also applicable to light frequencies.

In view of the utilitarian aspects of the processing compression block 320, in an exemplary embodiment, with reference to the methods of FIGS. 5-7, in an exemplary embodiment, the third operating regime utilizes a general compression strategy, such as, by way of example only and not by way of limitation, with respect to a hearing prosthesis, the ACE sound processing strategy. In this regard, the hearing prosthesis utilizes a processing strategy that corresponds to the typical processing strategy utilized by that prosthesis. That is, during normal operation (most operation), the hearing prosthesis will utilize this particular processing strategy. It is only when the recipient becomes fatigued that the processing strategy is changed or otherwise modified. In this regard, in an exemplary embodiment, the first operating regime can correspond to one that implements a modified ACE sound processing strategy, known in the art as the ACE with MP3 superscript 000 considerations, such as that detailed in U.S. Pat. No. 7,272,446 to John Parker, who at the time that the application was filed (Aug. 21, 2001, by way of the PCT, and Aug. 21, 2000, by way of the priority Australian patent application PQ 9528), performed his innovative work in Lane Cove, NSW, Australia, Mr. Parker being a citizen of Australia. In an exemplary embodiment, the first operating regime can correspond to one that implements any modified sound processing strategy relative to that which was utilized during the zero fatigue level/that of the third operating regime. Thus, the third operating regime with respect to methods 500-700 can utilize an unmodified ACE/pure ACE sound processing strategy. With respect to the methods where the sense prosthesis is operated according to a first operating regime that is different from the third operating regime while the recipient has a first fatigue level, this first operating regime can correspond to the above-noted modified ACE strategy/ACE with MP3 superscript 000 considerations. With respect to the methods where the sense prosthesis is operated according to the first operating regime while the recipient has a second fatigue level, this strategy is thus utilized while the recipient is at the second fatigue level. That said, in alternate embodiments, such as those that entail operating the sense prosthesis according to a second operating regime while the recipient has a second fatigue level, a more aggressive compression strategy than that which is achieved or otherwise utilized by the strategy implemented during the first operating regime can be utilized. By way of example, the first operating regime can utilize a "light" version of the ACE with MP3 superscript 000 considerations, and the second operating regime can utilize an "intense" or "aggressive" version of the ACE with MP3 superscript 000 considerations. Indeed, in some alternate embodiments, a completely different processing strategy can be implemented during the second operating regime providing that the teachings detailed herein and/or variations thereof can be practiced. Some additional details of such are described in greater detail below.

It is further noted that the masking models contemplated herein are not only dependent on different sound intensities, but also on spectral and temporal characteristics. Such spectral and temporal characteristics are, in some embodiments, defined in part by various adjustable parameters, such as by way of example only and not by way of limitation, spectral masking slopes, temporal masking offsets, and the number of spectral maxima.

With respect to the methods 500, 600, and 700 detailed above, the third operating regime can permit or otherwise will permit more spectral maxima than that of the first operating regime, and the first operating regime can permit or otherwise will permit more spectral maxima than that of the second operating regime. This can be done in a quantitative manner. In an exemplary embodiment, the third operating regime is an operating regime where the number of spectral maxima that are presented to the recipient is no more than 5, 6, 7, 8, 9, 10, 11, 12, 13, or 14, depending on the embodiment. Still further, in an exemplary embodiment, the first operating regime is an operating regime where the number of spectral maxima that are presented to the recipient is no more than 3, 4, 5, 6, 7, 8, or 9, depending on the embodiment. Also, in an exemplary embodiment, the second operating regime is an operating regime where the number of spectral maxima that are presented to the recipient is no more than 1, 2, 3, 4, 5, 6, or 7. In at least some exemplary embodiments, the spectral masking regulation block 330 is utilized to implement method 500, where there are three different operating regimes for the two levels of fatigue plus the zero level of fatigue. In this regard, in an exemplary embodiment, the operating regime for the zero level of fatigue can correspond to a limit of 8 spectral maxima, the operating regime for the first level of fatigue can correspond to a limit of 6 spectral maxima, and the operating regime for the second level of fatigue can correspond to a limit of four spectral maxima (in an exemplary embodiment). That said, in some alternate embodiments, the spectral masking regulation block 330 is utilized to implement method 600 and/or method 700, where there are 2 different operating regimes for the two levels of fatigue plus the zero level of fatigue.

Figure 9:
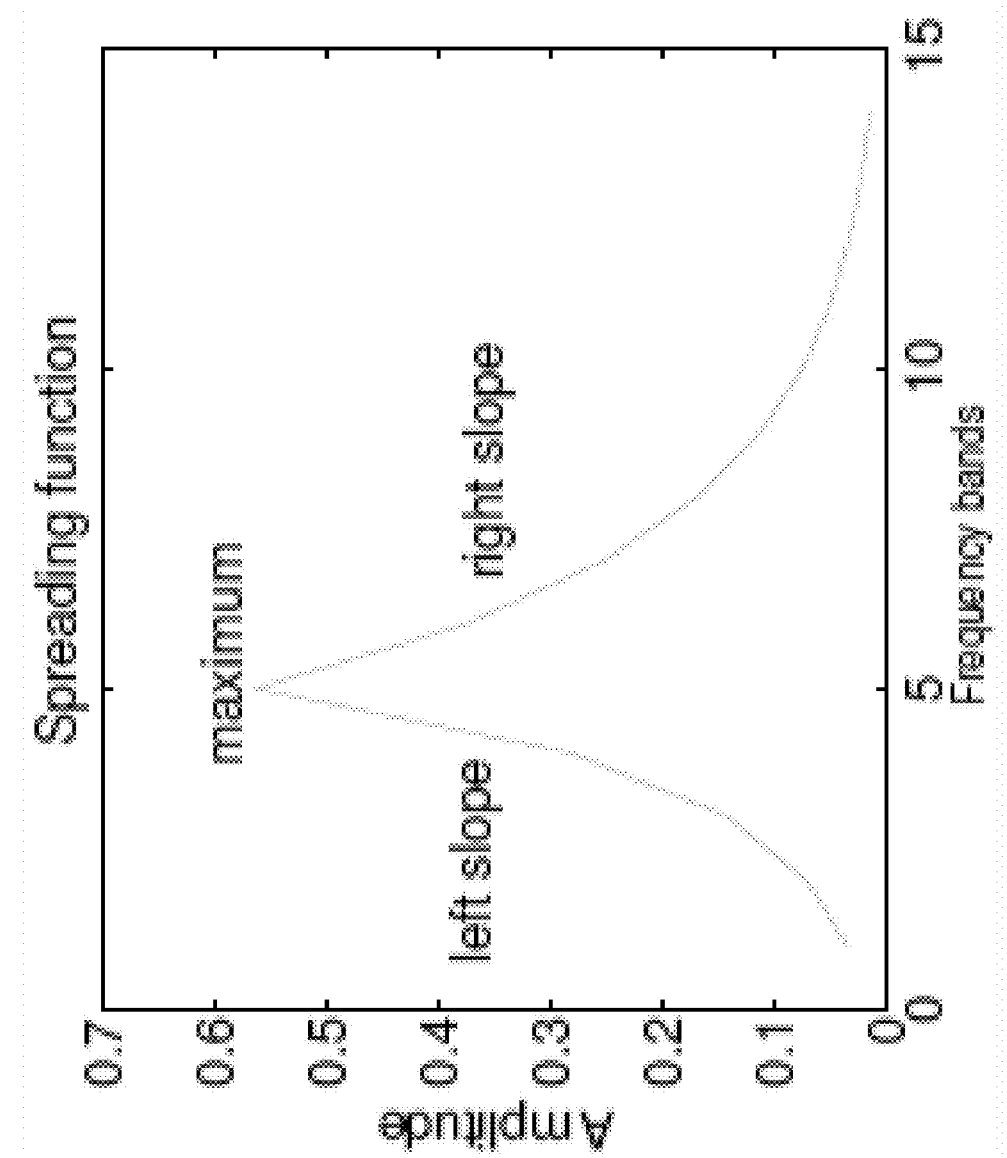
FIG. 9 presents an exemplary illustration of another exemplary phenomenon associated with an exemplary embodiment.

That said, in alternate embodiments and methods 400-700, the management of spectral maxima can be done in a manner that does not have a fixed quantitative value, but can achieve spectral masking based on the size of the given maxima. In this regard, as noted above, like 330, the spectral masking threshold regulation block. In this vein, output side processing 300 includes spectral masking threshold regulation block 330. The spectral masking threshold regulation block adjusts a slope of the masking (the masking slope) to impact frequencies that are at either higher or lower frequencies than an input at issue. FIG. 9 illustrates an example of how a left or lower frequency slope, and a right or higher frequency slope can be defined with respect to a given maxima (see also FIG. 8 and how the masking slope defines a masking threshold). Generally, a relatively more aggressive masking slope corresponds to a more gradual (or less steep slope), which in turn functions to eliminate more maxima from being encoded and provides a greater degree of masking. Accordingly, in an exemplary embodiment, the spectral masking threshold regulation block 330 regulates the masking slope that will be utilized with respect to the output side. In some exemplary embodiments, the prosthesis will be utilized in some scenarios to have a slope that is less steep, more gradual than that which was the case in other scenarios, thus eliminating spectral maximas that otherwise might be present with a steeper slope. Accordingly, in an exemplary embodiment, in a first operating regime, the spectral masking slope is greater (in absolute value) than that of the second operating regime, and the third operating regime utilizes a spectral masking slope that is greater than that of the first and second operating regimes. In an exemplary embodiment, the slope of the third operating regime is more than about 0.1, 0.15, 0.2, 0.25, 0.3, 0.4, 0.5, 0.75, 1.0, 1.25, 1.5, 1.75, 2.0, 2.25, 2.5, 2.75, 3, 3.5, 4, 4.5, 5, 5.5, 6 times, or more than that of the first operating regime, or any value or range of values therebetween in 0.01 increments, and the slope of the first operating regime is more than about 0.1, 0.15, 0.2, 0.25, 0.3, 0.4, 0.5, 0.75, 1.0, 1.25, 1.5, 1.75, 2.0, 2.25, 2.5, 2.75, 3, 3.5, 4, 4.5, 5, 5.5, 6 times, or more than that of the second operating regime, or any value or range of values therebetween in 0.01 increments.

Accordingly, in at least some exemplary embodiments, the third operating regime is an operating regime that results in a spectral masking slope of the prosthesis being steeper than that which is the case with respect to the first operating regime. Accordingly, in at least some exemplary embodiments, the first operating regime is an operating regime that results in a spectral masking slope of the prosthesis being steeper than that which is the case with respect to the second operating regime. That said, in some exemplary embodiments, the third operating regime is an operating regime that results in a spectral masking slope of the prosthesis that is the same as that which is the case with respect to the first operating regime, but those slopes are steeper than that which is the case with respect to the second operating regime. Still further, in some exemplary embodiments, the first and second operating regimes result in spectral masking slopes of the prosthesis that are the same, whereas the third operating regime results in spectral masking slopes of the prosthesis that are steeper than that of the first and second operating regimes. Also, in view of the above, it can be understood that the hearing prosthesis can operate an operating regime where the hearing prosthesis limits the number of spectral maxima in an output signal to a tissue stimulator that stimulates tissue to evoke a hearing and/or a vision percept relative to that which is the case in another operating regime.

Still further, with continuing reference to FIG. 3, as can be seen, output side processing 300 further includes a temporal masking regulation block 335. In this regard, in an exemplary embodiment, the prosthesis can vary the temporal masking offsets that are utilized during exemplary scenarios (which includes implementing embodiments where there is no temporal offset—it is noted that all of the examples herein include utilizing the prostheses without the implementation of a functionality of a given block—for example, there can be no processing compression, no spectral maxima regulation, no spectral masking threshold regulation, etc., in some scenarios).

More specifically, masking can also have a temporally forward and/or backward impact. Forward masking occurs when the sound following a masker cannot be heard, and backward masking occurs when a masker follows the sound. With respect to a hearing prosthesis, a forward masker generally impacts sound thresholds approximately 100-200 ms following the masker, and a backward masker generally impacts sound thresholds approximately 10 ms prior to the masker. Similar concepts are applicable for a vision prosthesis, such as a retinal implant. In this regard, a forward masking offset of 200-250 ms is greater than a forward masking offset of 100-200 ms, and thus will eliminate more following input than the latter, and a backward masking offset of 150 ms is greater than a backward masking offset of 100 ms, and thus will eliminate more prior input than the latter. Both latter offsets will result in less data being provided to the recipient of the output of the prosthesis than that which would be the case with respect to the respective former offsets.

In an exemplary embodiment implementing method 500, the third operating regime corresponds to that where the temporal masking offset is a zero temporal masking offset (there is no temporal masking offset). The first operating regime corresponds to that where the temporal masking offset is moderate, and the second operating regime corresponds to that where the temporal masking offset is aggressive, where the temporal offset for the moderate is smaller than that for the aggressive. In an exemplary embodiment, the offset utilized in the first operating regime corresponds to a temporal offset that is about 0.05, 0.1, 0.15, 0.2, 0.3, 0.4, 0.5, 0.6, 0.7, or 0.8 times the amount of that utilized in the second operating regime. With respect to embodiments that utilize only two operating regimes for the two levels of fatigue plus the zero level of fatigue, the moderate or the aggressive temporal masking offset can be utilized. In an exemplary embodiment, the temporal masking offset that is utilized in the binary operating regime embodiment can correspond to any of those detailed herein.

Note further that in at least some exemplary embodiments, depending on the scenario, forward masking and/or backward masking can be implemented without implementing the other. Still further, in an exemplary embodiment, aggressive backward masking can be utilized while at the same time moderate forward masking can be utilized, and vice versa. Any combination of the temporal masking offset implementations can be utilized in at least some exemplary embodiments corresponding to operating regimes that relate to fatigue level. Note further, that in at least some exemplary embodiments, an operating regime implemented at the zero fatigue level (e.g., the third operating regime) can include some temporal masking offset. In an exemplary embodiment, the temporal masking offset is less than (the time is not as great) as those of the other two operating regimes. In an exemplary embodiment, the temporal masking offset used during the third operating regime is about 0.01, 0.02, 0.03, 0.04, 0.05, 0.075, 0.1, 0.125, 0.15, 0.175, 0.2, 0.25, 0.3, 0.35, 0.4, 0.5, 0.6, 0.7, or 0.8 the temporal length of the first operating regime and/or in the second operating regime.

Again continuing with reference to FIG. 3, output side processing 300 further includes spectral maxima regulation block 325. While the processing compression block 320 does result in fewer maxima due to the reduction in processing, embodiments, also can artificially limit the number of maxima of the given processing compression strategy resulting from block 320, relative to that which would be the case in the absence of maxima regulation. In an exemplary embodiment, fewer maxima results in less stimulation relative to that which would be the case with more maxima, all other things being equal.

Accordingly, in an exemplary embodiment, the prosthesis can be operated in a regime where the number of spectral maxima is limited relative to that which is the case with respect to operation during other scenarios.

As noted above, some exemplary embodiments utilize noise cancellation techniques in the input side of the processing. Conversely, embodiments can also utilize and/or instead utilize noise mitigation techniques on the output side. With continued reference to FIG. 3, it can be seen that the output side processing 300 further includes qualitative output data management block 340. In this regard, block 340 implements or otherwise provides stimulus mitigation/stimulus reduction in the form of stimulus reduction algorithms. In an exemplary embodiment, these stimulus reduction algorithms can reduce the amount of stimulus based on light that is captured that is provided to the recipient. In this regard, embodiments include light mitigation/light reduction algorithms. With respect to hearing prostheses, some exemplary embodiments include sound mitigation algorithms and sound reduction algorithms. It is noted that in general, the processing strategies in at least some exemplary embodiments that are directed to a hearing prosthesis, irrespective of the presence of block 340, employ a brightening (high-pass) filter to suppress low-frequency audio information. That said, in some exemplary embodiments, block 340 can implement adaptive dynamic range optimization to focus processing on sound intensities that have a higher probability of being associated with sound that is deemed to be desired. With respect to vision prostheses, the processing strategy can also include a brightening strategy and/or a darkening strategy, with similar conceptual results. That said, in some exemplary embodiments, block 340 can implement adaptive dynamic range optimization to focus processing on light intensities that have a higher probability of being associated with light that is deemed to be desired.

In view of the above, in an exemplary embodiment, the first operating regime corresponds to an operating regime where the prosthesis is operated such that there is more noise mitigation than that which results in the third operating regime. Still further, in an exemplary embodiment, the second operating regime corresponds to an operating regime where the prosthesis is operated such that there is more noise mitigation than that which results in the first operating regime (and thus more noise mitigation than that which results in the third operating regime). That said, in some exemplary embodiments, the noise mitigation that results in the operation of the prosthesis in the first and second operating regimes is the same, but more so than that of the third operating regime. Corollary to this is that in some exemplary embodiments, the noise mitigation that results in the operation of the prosthesis at the first and third operating regimes is the same, but less so than that of the second operating regime. Note that with respect to embodiments where there is disclosure of the various results being the same (e.g., noise mitigation being the same), these are disclosed in terms of relative samity. That is, all things being equal, the result is the same. Accordingly, for the same captured environmental phenomenon (light, sound), the noise mitigation, for example, is the same, or more accurately, the prosthesis operates such that the noise mitigation should be the same.

Thus, in an exemplary embodiment, such as an embodiment where the ambient environment is bright (in the light sense) and/or noisy (in the sound sense), block 340 is utilized to focus processing on light and/or sound intensities that have a higher probability of being associated with moving objects, for example, and with speech, respectively, for example, depending on the type of prosthesis in which the teachings detailed herein are implemented.

It is noted that block 340 is differentiated from the other types of light and noise reduction that can achieve by single cancellation, or the other types of light and noise management that can be achieved by, for example, beamforming, both of which are associated with input side of the processing.

Accordingly, in an exemplary embodiment, block 340 is utilized in different manners depending on the given fatigue level or lack thereof of the recipient. In an exemplary embodiment, noise mitigation applied during the third operating regime is a standard noise mitigation implementation, although in some other embodiments, the third regime entails no noise mitigation (on the output side—this can still be present on the input side). Still further, in an exemplary embodiment, noise mitigation applied during the first operating regime is a moderate noise mitigation as compared to that applied during the third operating regime. It is noted that in some embodiments where the recipient is at the second fatigue level, the moderate noise mitigation is utilized as well. Conversely, in some alternate embodiments, where the recipient is at the second fatigue level, as well as the first fatigue level, the aggressive noise mitigation implementation is utilized. That said, in some alternate embodiments, no noise mitigation or standard noise mitigation is utilized while at the zero fatigue level and at the first fatigue level, and the moderate or aggressive noise mitigation is utilized at the second fatigue level.

It is briefly noted at this time that while the embodiments detailed above have focused on the utilization of three different levels—two levels of fatigue in a zero level of fatigue, in an alternate embodiment, there can be four different levels or more. For example, in a method where the recipient is at a third level of fatigue greater than that of the second and first levels of fatigue, the aggressive noise mitigation can be used, while the moderate noise mitigation was utilized at the second level of fatigue, and the standard level of noise mitigation was utilized at the first level of fatigue, and no mitigation of noise was utilized at the zero level of fatigue. Alternatively, a standard can be utilized at the zero level of fatigue, a moderate noise mitigation can be used at the first and second levels of fatigue, and the aggressive noise mitigation can be utilized at the third level of fatigue.

In the embodiment represented by FIG. 3, in some exemplary embodiments, the output side processing 300 further includes a relative data management block 345. In an exemplary embodiment, relative data management block 345 manages the output of the hearing prosthesis, or more accurately, processes on the output side the output of the hearing prosthesis such that the output is relativized. By way of example only and not by way of limitation, embodiments can utilize light growth and loudness growth functions. With respect to loudness growth (identified as the Q factor in the art), loudness growth defines how the acoustic dynamic range is mapped into electric output. This corresponds to the role acoustic dynamic range that the processing can optimize. However, in at least some exemplary embodiments, when Q values increase, more information is mapped onto the audible levels. This can entail increasing the amount of "noisy" information that is mapped onto the audible levels. In at least some exemplary embodiments, this can have a deleterious effect in that the noisy information can crowd out the information that is wanted or otherwise desirable, or can crowd out information that is more wanted or otherwise more desirable relative to the additional information that is inputted into the audible spectrum. A similar concept applies to vision prostheses where an increase in brightness can crowd out information that is more desirable and more useful to the recipient relative to the additional information that is inputted due to the increase in brightness.

Accordingly, in an exemplary embodiment, block 345 changes the Q value of the hearing prosthesis depending on given scenarios. By way of example only and not by way of limitation, in an exemplary embodiment, in a scenario where the recipient is utilizing the hearing prosthesis while at a zero level of fatigue, the third operating regime can entail operating the hearing prosthesis with a Q value of for example 10, which is typically what is utilized in a standard quiet setting. In an exemplary embodiment, the Q value of the third regime can be or is less than 5, 6, 7, 8 9, 10, 11, 12, 13, 14, 15, 16, 17, 18, 19, 20, or any value or range of values therebetween.

Still further by way of example only and not by way of limitation, in an exemplary embodiment, in a scenario where the recipient is utilizing the hearing prosthesis while at a first level of fatigue, the first operating regime can entail operating the hearing prosthesis with a Q value of, for example, 20, which is typically what is utilized in a standard noisy setting. In an exemplary embodiment, the Q value of the first regime can be or is less than 15, 16, 17, 18, 19, 20, 21, 22, 23, 24, 25, 26, 27, 28, 29, or 30 or any value or range of values therebetween. Still further by way of example only and not by way limitation, in an exemplary embodiment, in a scenario where the recipient is utilizing the hearing prosthesis while at a second level of fatigue, the second operating regime can entail operating the hearing prosthesis with a Q value of for example 30, which is typically what is utilized in a very noisy setting. In an exemplary embodiment, the Q value of the first regime can be or is less than 20, 21, 22, 23, 24, 25, 26, 27, 28, 29, 30, 31, 32, 33, 34, 35, 36, 37, 38, 39, or 40, or any value or range of values therebetween.

Thus, in view of the above, in an exemplary embodiment, the hearing prosthesis is configured to operate in an operating regime where a Q factor of the prosthesis is larger relative to that which is the case in another operating regime.

Still further with respect to FIG. 3, the output side processing 300 further includes channel emphasis block 350. As noted above, in some exemplary embodiments of the prostheses detailed herein and/or variations thereof, the input is divided up into channels, such as by way of example, by the filter block. Channel emphasis block 350 can emphasize some of these channels over others. Indeed, in an exemplary embodiment, channel emphasis block 350 emphasizes some channels by eliminating other channels, or more specifically, eliminating the output of one or more given channels from the output of the output side processing 300. Still further, in an exemplary embodiment, channel emphasis block 350 can emphasize some channel(s) by reducing the magnitude/amplitude of the output signal of some channel(s) relative to others, instead of eliminating those channel(s) entirely. Corollary to this is in that in at least some exemplary embodiments, channel emphasis block 350 can emphasize some channels by increasing the magnitude/amplitude of the output signal of some channel(s) relative to others, all other things being equal.

In an exemplary embodiment, there can be scenarios where the information on one or more given channels is deemed more useful to a recipient then information on one or more other channels. However, the information on the one or more other channels makes it more difficult to understand the information on the one or more channels where the information is deemed more useful, at least relative to the scenario where if the information in those other channels that is deemed not as useful were not present. Accordingly, in an exemplary scenario, channel emphasis block 350 can be utilized to operate the hearing prosthesis such that one or more channels are emphasized over one or more other channels (which includes deemphasizing, including eliminating, channels) with respect to the output of the output side processing 300.

Accordingly, in an exemplary embodiment, block 350 is utilized in different manners depending on the given fatigue level or lack thereof of the recipient. In an exemplary embodiment, channel enhancement applied during the third operating regime is a standard channel enhancement implementation, although in some other embodiments, the third regime entails no channel enhancement whatsoever (on the output side—this can still be present on the input side). Still further, in an exemplary embodiment, channel enhancement applied during the first operating regime is a moderate channel enhancement as compared to that applied during the third operating regime. In an exemplary embodiment, during the first operating regime, one or two channels may be eliminated, whereas only one channel or no channels may have been eliminated during the third operating regime.

It is noted that in some embodiments where the recipient is at the second fatigue level, the moderate channel enhancement regime is utilized as well. Conversely, in some alternate embodiments, where the recipient is at the second fatigue level, as well as the first fatigue level, the aggressive channel enhancement implementation is utilized. (In an exemplary embodiment, aggressive channel enhancement can entail cancelling more channels than that which was the case in the moderate channel enhancement.) That said, in some alternate embodiments, standard channel enhancement or no channel enhancement is utilized while at the zero fatigue level and at the first fatigue level, and the moderate or aggressive channel enhancement is utilized at the second fatigue level.

While the above exemplary embodiment has focused on the elimination of channels, in an alternate embodiment, standard channel enhancement (such as that which can correspond to that utilize during the third operating regime) can entail amplifying certain channels by a first amount relative to others, moderate channel enhancement can entail amplifying certain channels by a second amount relative to others different than the first amount (which includes amplifying some channels less than that which was the case during the standard channel enhancement), and can in fact entail amplifying certain channels by a second amount relative to others while canceling other channels entirely, etc.

In view of the above, in an exemplary embodiment, the hearing prosthesis can be operated in an operating regime where the hearing prosthesis limits a resulting perceptual frequency relative to that which is the case in another operating regime.

As noted above, the present teachings have been described in terms of a sense prosthesis in general, and a hearing prosthesis and a vision prosthesis, in particular. Still further, embodiments are directed towards implantable prostheses, as distinguished from, for example, non-implanted prostheses. For example, a pair of glasses or a conventional hearing aid corresponds to a non-implantable prosthesis. Corollary to this is that in at least some exemplary embodiments, the teachings detailed herein and/or variations thereof are implemented with recipients that are clinically and/or legally blind and/or deaf, as those phrases have meaning as of Mar. 15, 2016, in any one of the United States, Canada, any given country that is a member of the European Patent Convention, Japan, the People's Republic of China, the Republic of Korea, as the case may be with respect to the filing of this application. Still further, the teachings detailed herein and/or variations thereof are implemented with recipients that are U.S. Social Security Administration Classified as legally blind and/or deaf, as those phrases have meaning as of Mar. 15, 2016, with respect to the Social Security Administration of the United States of America. That is, the teachings detailed herein are implemented in recipients that meet the requirements for obtaining Social Security benefits because the recipient is legally deaf and/or legally blind.

Thus, the embodiments of a pair of glasses and a conventional hearing aid have little, if any, utilitarian value with respect to such recipients, at least with respect to evoking a vision percept and/or evoking a hearing percept.

Figure 10:
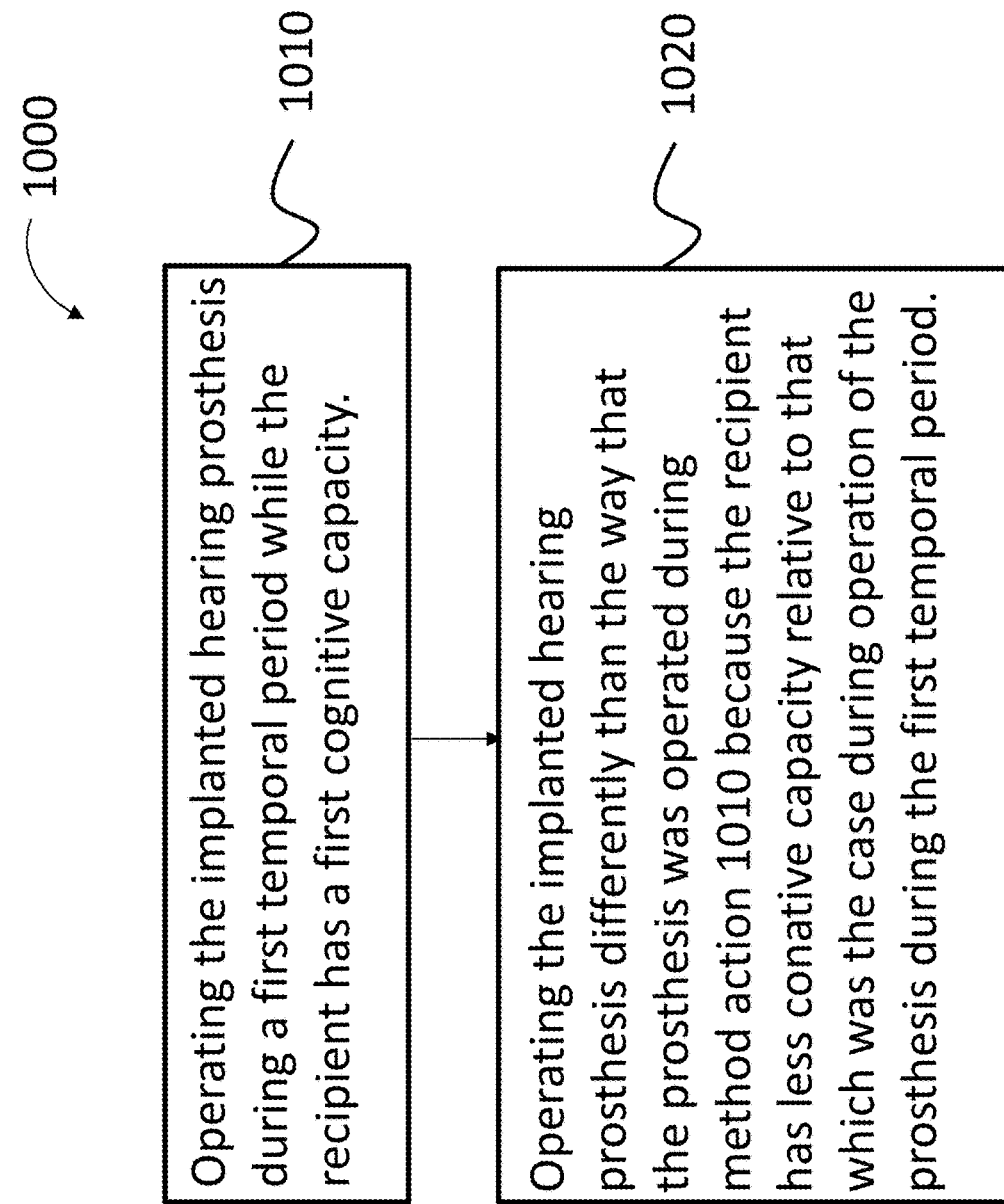
FIG. 10 presents another exemplary flowchart for an exemplary method according to an exemplary embodiment.

Thus, at least some exemplary embodiments are directed towards implementing any or all of the teachings detailed herein with respect to an implantable device. Accordingly, FIG. 10 depicts an exemplary method 1000 of operation of a implanted prosthesis, such as a retinal implant, a cochlear implant, a middle ear implant, or a bone conduction implant (including those that have a vibrator located outside the recipient but a component that is implanted beneath the skin of the recipient/inside the recipient). The method 1000 includes method action 1010, which entails operating the implanted hearing prosthesis during a first temporal period. Method 1000 further includes method action 1020, which entails, in a second temporal period subsequent to the first temporal period, operating the implanted hearing prosthesis differently than the way that the prosthesis was operated during the first temporal period, because the recipient has less conative capacity relative to that which was the case during operation of the prosthesis during the first temporal period.

By way of example only and not by way of limitation, a cognitive capacity can correspond to the ability of the recipient to understand implant evoked speech percepts, all things being equal. That said, in some alternate embodiments, a cognitive capacity can correspond to the ability of the recipient to understand implant evoked speech percepts, under the influence of a given environmental stimulus, and such can be relative to the ability of the recipient to do this without the influence of the given environmental stimulus, all other things being equal. Thus, cognitive capacity can be a function of fatigue, and cognitive capacity can also be a function of the environment. For example, a recipient under the influence of caffeine, alcohol, or drugs, including but not limited to prescription drugs, can have a cognitive capacity that is different than that of the exact same recipient utilizing the exact same hearing prosthesis, all other things being equal. Still further, environmental conditions are not limited to conditions that are directly mind altering. In an exemplary embodiment, environmental conditions that can affect cognitive ability include heat, cold, a distracting environment (loud noises, a person one finds attractive being in visual range in a manner that makes clear reasons for the attraction, distracting actions occurring, such as large protests against political leaders, etc.). Indeed, as can be understood, cognitive capacity can be unrelated to fatigue—the caffeine example can render the recipient unfatigued. Note further that in exemplary embodiments, cognitive capacity can be influenced by both the environment and fatigue. Also, cognitive capacity can be influenced by psychological conditions that are not induced by environment. A completely unfatigued recipient (one at the zero level of fatigue) who is completely isolated from outside stimuli at the current time can still have reduced cognitive abilities relative to other temporal periods because he or she is simply having "a bad day." Any scenario that can result in diminished cognitive capacity with respect to the ability of the recipient to perceive or otherwise understand the content of the evoked hearing percepts can be a stimulus for such.

At this time it is noted that in an exemplary embodiment, the varying of the aforementioned operating regimes can have utilitarian value with respect to reducing the cognitive load applied to the recipient vis-à-vis the evoked hearing percepts for a given amount of content extraction there from. Still further, the varying of the aforementioned operating regimes can have utilitarian value with respect to accommodating the recipient as the recipient becomes more fatigued. With respect to utilizing different processing strategies, ACE vs. ACE with MP3 subscript 000 vs. some other processing strategy, the processing strategy that will be utilized will be the one that is easier to use relative to that which is the case for the other fatigue levels, even though the content may not be as "good" as that which might otherwise be the case.

With respect to the embodiments detailed above with respect to various levels of fatigue and lack of a level of fatigue, any method detailed above that utilizes fatigue and/or lack of a fatigue as a scenario qualifier can be transposed to methods that utilize cognitive level as a scenario qualifier. By way of example only and not by way of limitation, with respect to the method 500, the first fatigue level can correspond to a first diminished cognitive level where the cognitive capacity to understand or otherwise comprehend the information embodied in the evoked hearing percept and/or visual percepts relative to that which is the case a prior temporal period. Accordingly, zero fatigue level can be transposed to a zero diminished cognitive capability level. On the opposite end of the spectrum, the second fatigue level can correspond to a diminished cognitive capacity to understand or otherwise comprehend the information embodied in the evoked hearing percept and/or visual percepts relative to that which was the case at the first diminished cognitive level. This is not to say that as used herein diminished cognitive capacity corresponds to fatigue. Just the opposite. As detailed above, diminished cognitive capacity can exist without fatigue. Accordingly, the two are different. The transposition with respect to cognitive capacity and fatigue is simply presented in a manner that is shorthand for what otherwise would correspond to the above disclosures associated with methods 400-700 being repeated below in terms of cognitive capacity as opposed to fatigue. Thus, for purposes of shorthand, the disclosure herein of a first operating regime corresponds to operating the prosthesis such that the information provided to the recipient takes less cognitive capacity to process than that which is the case when the prosthesis is operated during at the third operating regime, all things being equal. Still further, for the purposes of shorthand, the disclosure herein of a second operating regime corresponds to operating the prosthesis such that information provided to the recipient takes less cognitive capacity to process than that which is the case with respect to when the prosthesis is operated at the first operating regime, all things being equal, and visa-versa. Still further, for the purposes of shorthand, the disclosure herein of the first fatigue level corresponds to a first cognitive capability level, the disclosure herein of the second fatigue level corresponds to a second cognitive capability that is lower than that of the first cognitive capability, and the disclosure herein of the zero fatigue level corresponds to a cognitive capability level that is maximum relative to the other levels. Again, this is simply for purposes of shorthand. This is not to say that they are the same. This simply eliminates the need to reproduce much of the above in terms of cognitive capability.

It is noted that some embodiments correspond to utilizing the embodiments detailed herein with respect to a cochlear implant. It is further noted that some exemplary embodiments correspond to utilizing the embodiments detailed with respect to a retinal implant.

Figure 11:
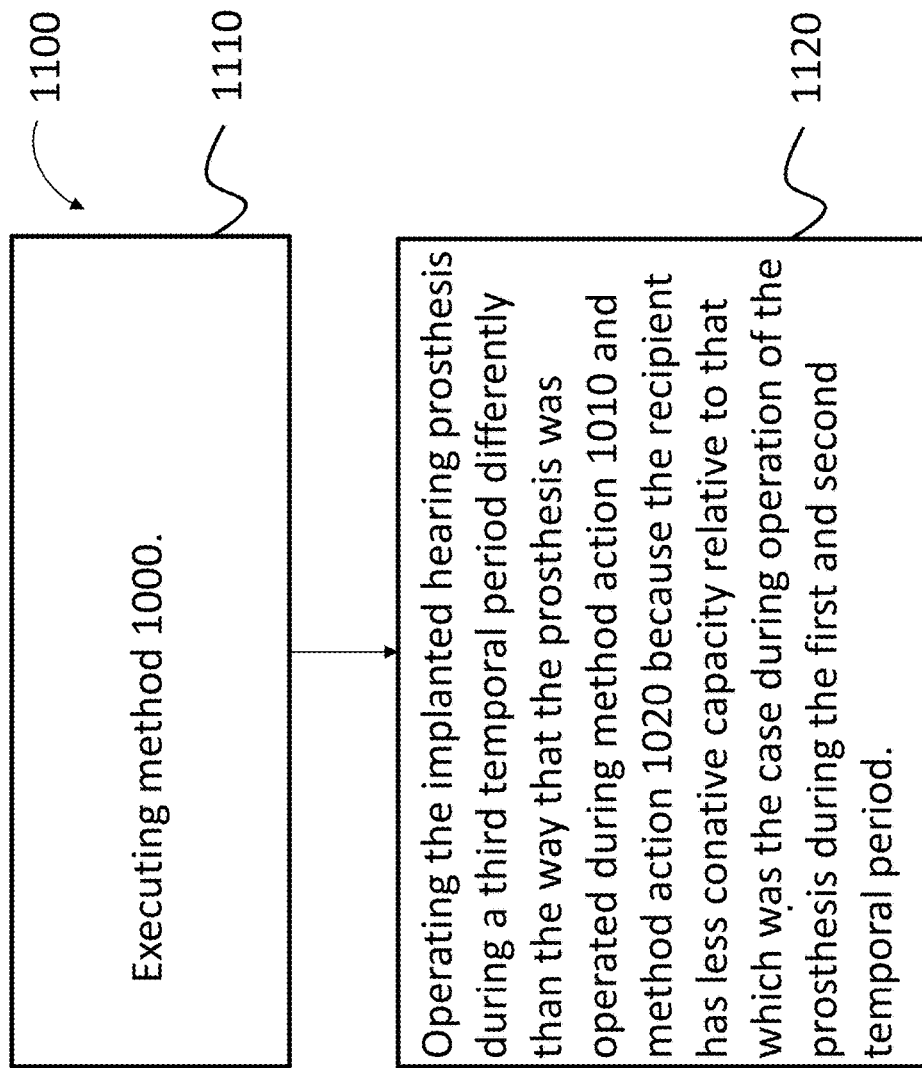
FIG. 11 presents another exemplary flowchart for an exemplary method according to an exemplary embodiment.

To be clear, while the embodiments of method 1000 detail two different temporal periods in a manner analogous to the method 400 detailed above, other embodiments can include three different temporal periods where each respective temporal period includes a cognitive capacity that is different from the other, and where each temporal period following the other results in a level of cognitive capacity that is lower than that which was the case during the prior temporal period. In this regard, FIG. 11 presents method 1100. Method 1100 includes method action 1110, which entails executing method 1000. Method 1100 further includes method action 1120, which entails operating the implanted hearing prosthesis differently during a third temporal period than the way the prosthesis was operated during method action 1010 and method action 1020, because the recipient has less cognitive capacity relative to that which was the case during operation of the prosthesis during the first and second temporal periods of method 1000. Accordingly, this can entail the juxtaposition of the second fatigue level in the teachings detailed above with the cognitive capabilities of the temporal period detailed in method 1120.

In an exemplary embodiment, with respect to method 1000, the first temporal period and the second temporal period at least have portions that fall within the same eight hour period. Note further that with respect to the third temporal period of method 1100, that third temporal period can also have portions that fall within the same eight hour period (which would mean that all of the second temporal period falls within that eight hour period. That said, instead of an eight hour period, embodiments can include a 16 hour temporal period or a 24-hour temporal period or a 48 hour period in which portions of the aforementioned temporal periods fall within.

It is noted that, for the purposes of shorthand, the disclosure herein of the recipient having various fatigue levels and the zero fatigue level corresponds to respective temporal periods of the method 1100. This is not to equate the two groups. This is only to avoid repeating swaths of text in terms of the features of methods 1000 and 1100.

Corollary to the aforementioned shorthand statements is that the above shorthand regimes also apply in reverse. For example, any disclosure herein of a given temporal period corresponds to the corresponding fatigue levels and the zero fatigue levels, where the zero fatigue level corresponds to the first temporal period, the first fatigue level corresponds to the second temporal period, and the second fatigue level corresponds to the third temporal period.

It is noted that the embodiments of methods 1000 and 1100 can be implemented with respect to operating the prosthesis differently, even though the cognitive capacity of the recipient has not been changed. In this regard, in an exemplary embodiment, during the first temporal period, an environment of the recipient changes. By way of example only and not by way of limitation, in an exemplary embodiment, the room in which the recipient is positioned becomes noisier. Still further by way of example only and not by way of limitation, in an exemplary embodiment, a speaker to which the recipient is focusing his or her attention stops speaking, and that speaker is replaced by another speaker who speaks in a manner that is not as clear as the original speaker. In an exemplary embodiment of method 1000, during a third temporal period (not to be confused with the above noted third temporal periods, as this is with respect to a method that has not encountered a third temporal period—again, these are naming conventions only) after the change in the environment, the method includes the action of operating the implanted hearing prosthesis differently than the way the prosthesis was operated before the environment of the recipient changed. Again, in this embodiment, the cognitive capacity of the recipient is that of the first cognitive capacity during the third temporal period. In an exemplary embodiment, the operation of the prosthesis can be such that the prosthesis is operated according to any of the first and second regimes detailed above relative to the third regime detailed above. Thus, an embodiment entails adjusting or otherwise changing the operation of the hearing prosthesis even though the cognitive capacity of the recipient has not changed. Still, in this embodiment, this is coupled with a corollary adjustment or otherwise change in the operation of the hearing prosthesis, because the cognitive capacity of the recipient has changed. Still further, while this embodiment focuses on the change in the environment during the first temporal period, in another embodiment, this can include a change in the environment during the second temporal period where the cognitive capabilities of the recipient have not changed. Note further that the scenario can occur during the first temporal period and during the second temporal period and during the third temporal period (with respect to method 1100), for that matter. Accordingly, in an exemplary embodiment, the recipient might find himself or herself adjusting the prosthesis so that it takes less cognitive effort to understand, at least in general terms, the information that is contained in the hearing percept and/or in the visual percept as the case may be, five times or more.

That said, in at least some exemplary embodiments, with respect to the third temporal period resulting from the environmental change detailed above, in an exemplary embodiment, the operation of the hearing prosthesis during the third temporal period is the same as the operation of the hearing prosthesis during the second temporal period. This can be, for example, the case in the scenario where at least one of prior to the beginning of the second temporal period or during the second temporal period, the environment of the recipient changes back to that which was the case during the first temporal period. For example, the scenario can include a situation where the cognitive capabilities of the recipient do decline, but for example, the speaker who is more difficult to understand has stopped speaking, and the speaker who is less difficult to understand has commenced speaking again. Thus, even though the recipient has less capability to understand what is being said, because the speech is clear, the recipient need not, or otherwise does not, find it utilitarian to compensate for his or her declining cognitive capabilities by operating the hearing prosthesis in a different manner.

Note that in keeping with the utilization of shorthand to reduce the amount of text in this application, this concept also corresponds to a scenario where the recipient remains at a first level of fatigue, a second level of fatigue, or a zero level of fatigue, but the environment changes while at these various levels of fatigue and/or the zero level of fatigue.

Figure 12:
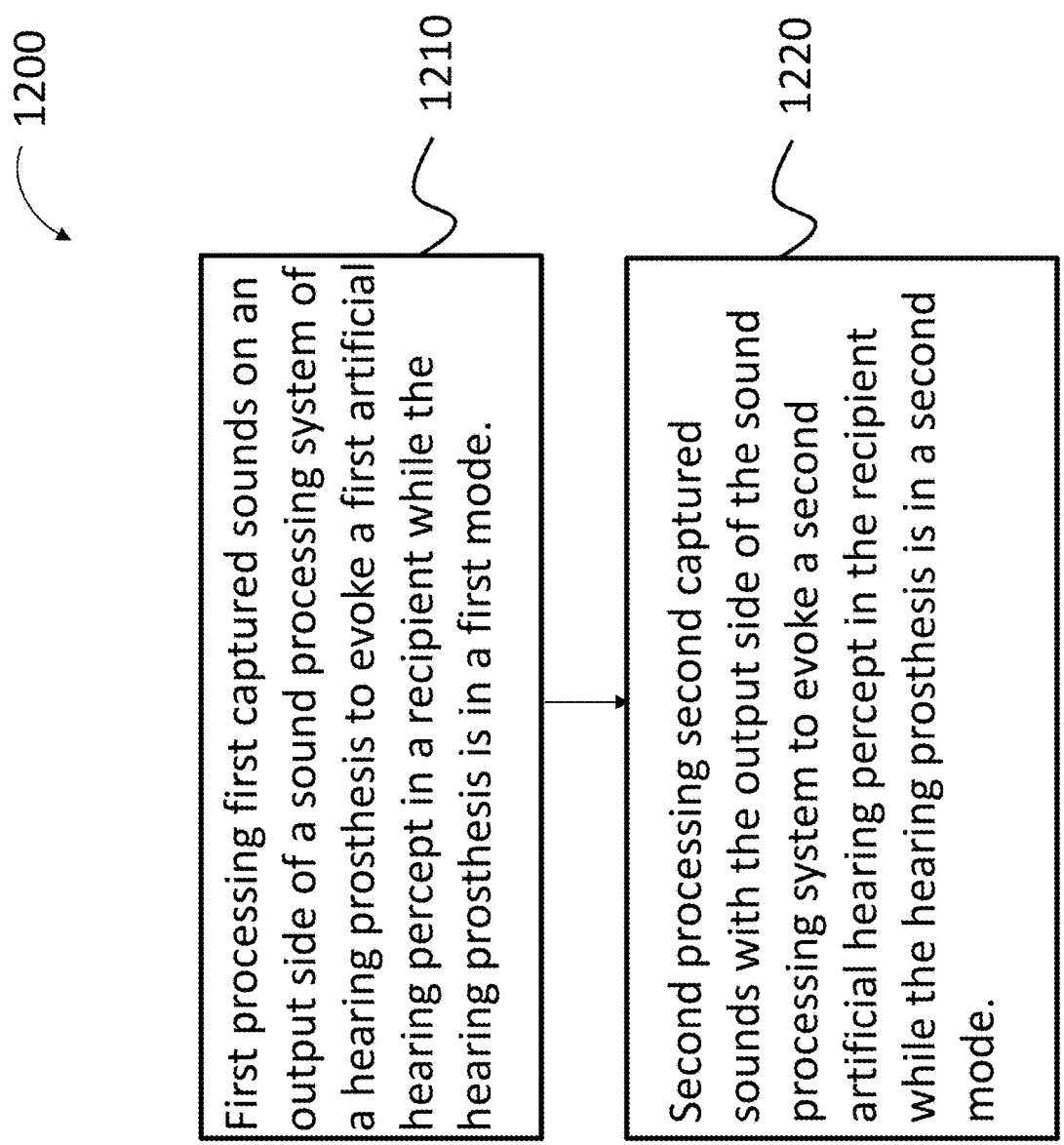
FIG. 12 presents another exemplary flowchart for an exemplary method according to an exemplary embodiment.

FIG. 12 presents another exemplary embodiment of an exemplary method, method 1200. Method 1200 includes method action 1210, which entails processing first captured sounds on an output side of a sound processor (e.g., that of output side processing 300 of FIG. 3) of a hearing prosthesis to evoke a first artificial hearing percept in a recipient while the hearing prosthesis is in a first mode. Method 1200 further includes method action 1220, which entails second processing second captured sounds with the output side of the sound processor to evoke a second artificial hearing percept in the recipient while the hearing prosthesis is in a second mode. In the embodiment of method 1200, all things being equal, the second processing is such that the recipient must devote less effort to generally understand the captured sounds than that which is the case with the first processing. It is noted that with respect to less effort, this is a relative phrase because it is qualified by the all things being equal caveat. In this regard, if the recipient had the same cognitive capability during the period of the first processing and the second processing, less effort would be required to generally understand the second processing (or more accurately, the hearing percept that is evoked due to the second processing). This means that in an exemplary embodiment, the recipient may still have to devote more effort to understanding the hearing percept than that which was the case with respect to the hearing percepts resulting from the first sound processing, such as by way of example that which may be the case with respect to the fact that the cognitive capabilities of the recipient have decreased from the first artificial hearing percept and the second artificial hearing percept or by that which may be the case with respect to the fact that the recipient has grown more fatigued etc. With respect to method 1200, it is just that if the recipient had the same level of fatigue with the same cognitive capabilities at the times that the first and second artificial hearing percepts were evoked, the recipient would have to devote less effort to generally understanding the captured sounds.

In an exemplary embodiment, the first mode can correspond to the third operating regime, and the second mode can correspond to the first or second operating regimes detailed above. In some alternative embodiments, the first mode can correspond to the first operating regime, and the second mode can correspond to the second operating regime.

Figure 13:
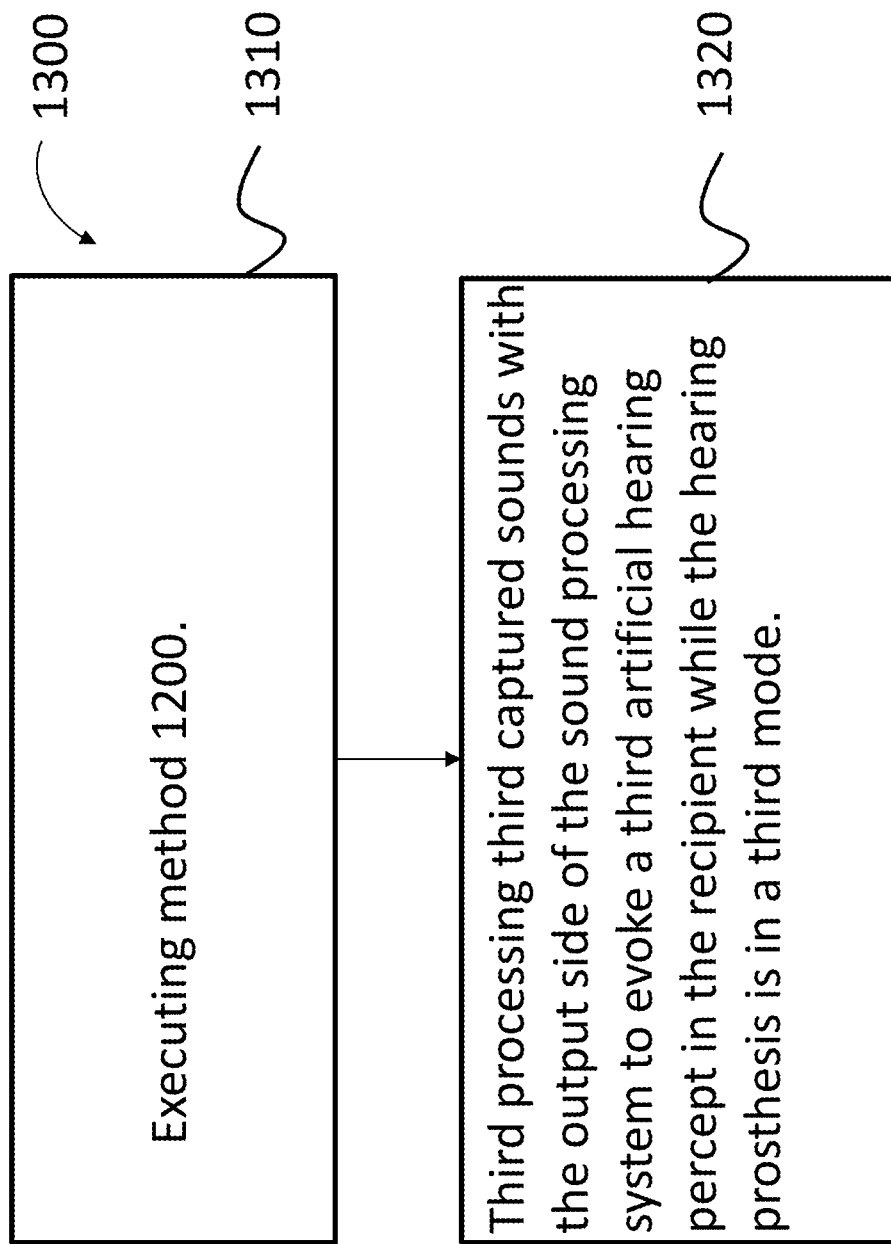
FIG. 13 presents another exemplary flowchart for an exemplary method according to an exemplary embodiment.

FIG. 13 represents another method, method 1300, corresponding to an exemplary embodiment. Method 1300 includes method action 1310, which entails executing method 1200. Method 1300 further includes method action 1320, which entails third processing third captured sounds with the output side of the sound processing system of the hearing prosthesis to evoke a third artificial hearing percept in the recipient while the hearing prosthesis is in a third mode. To be clear, it is noted that the aforementioned second mode and the aforementioned third mode are different from each other, and are different than the aforementioned first mode. In an exemplary embodiment, the second mode corresponds to the first operating regime, the third mode corresponds to the second operating regime, and the first mode corresponds to the third operating regime. In an exemplary embodiment, all things being equal, the third processing is such that the recipient must devote less effort to generally understand the captured sounds than that which is the case with the second processing.

Figure 14:
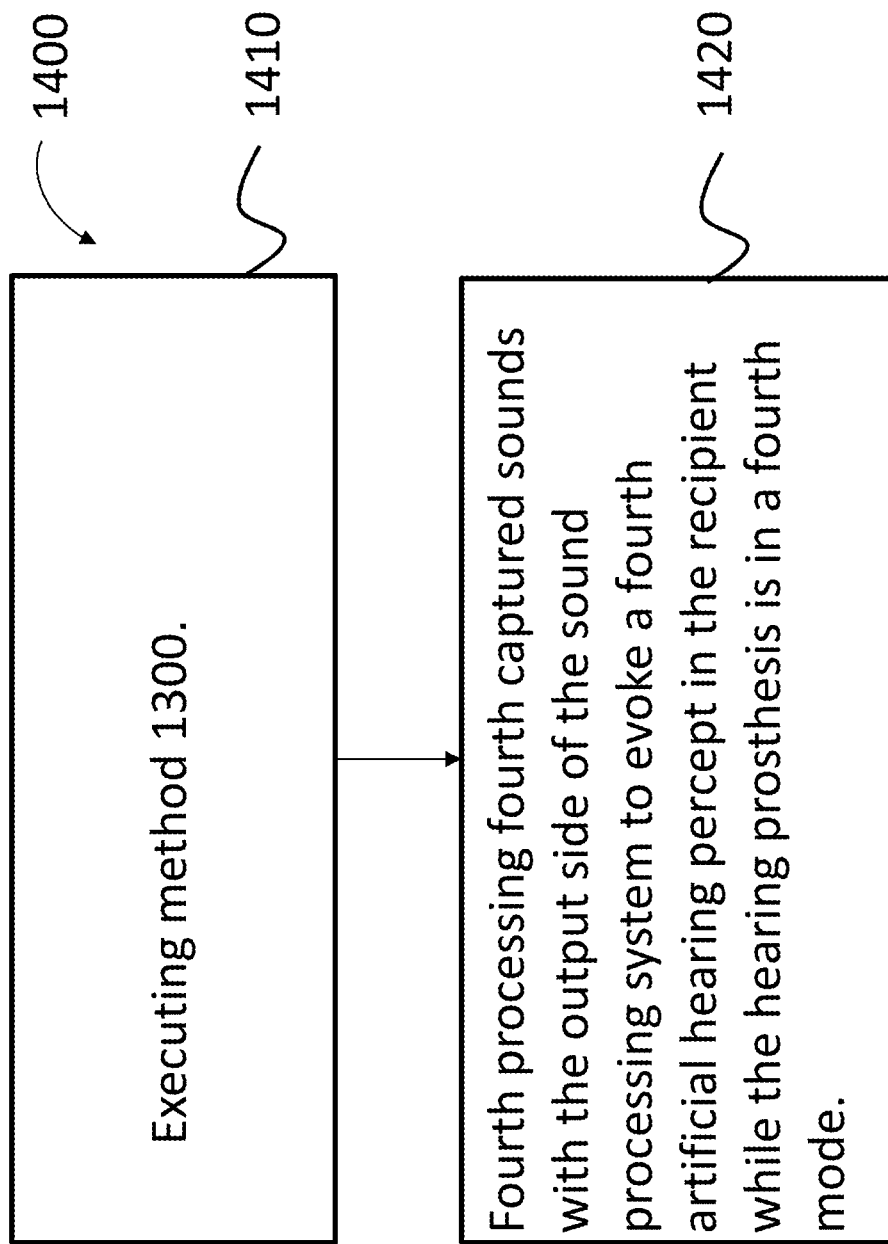
FIG. 14 presents another exemplary flowchart for an exemplary method according to an exemplary embodiment.

FIG. 14 represents another method, method 1400, corresponding to an exemplary embodiment. Method 1400 includes method action 1410, which entails executing method 1300. Method 1400 further includes method action 1420, which entails fourth processing fourth captured sounds with the output side of the sound processing system of the hearing prosthesis to evoke a fourth artificial hearing percept in the recipient while the hearing prosthesis is in a fourth mode. In an exemplary embodiment, all things being equal, the fourth processing is such that the recipient must devote less effort to generally understand the captured sounds than that which is the case with the third processing.

It will be understood that embodiments of the methods detailed herein can include repeating method 1400 to evoke a fifth captured hearing percept utilizing fifth processing, etc. where the fifth processing requires less effort than the fourth processing all things being equal, etc.

Figure 15:
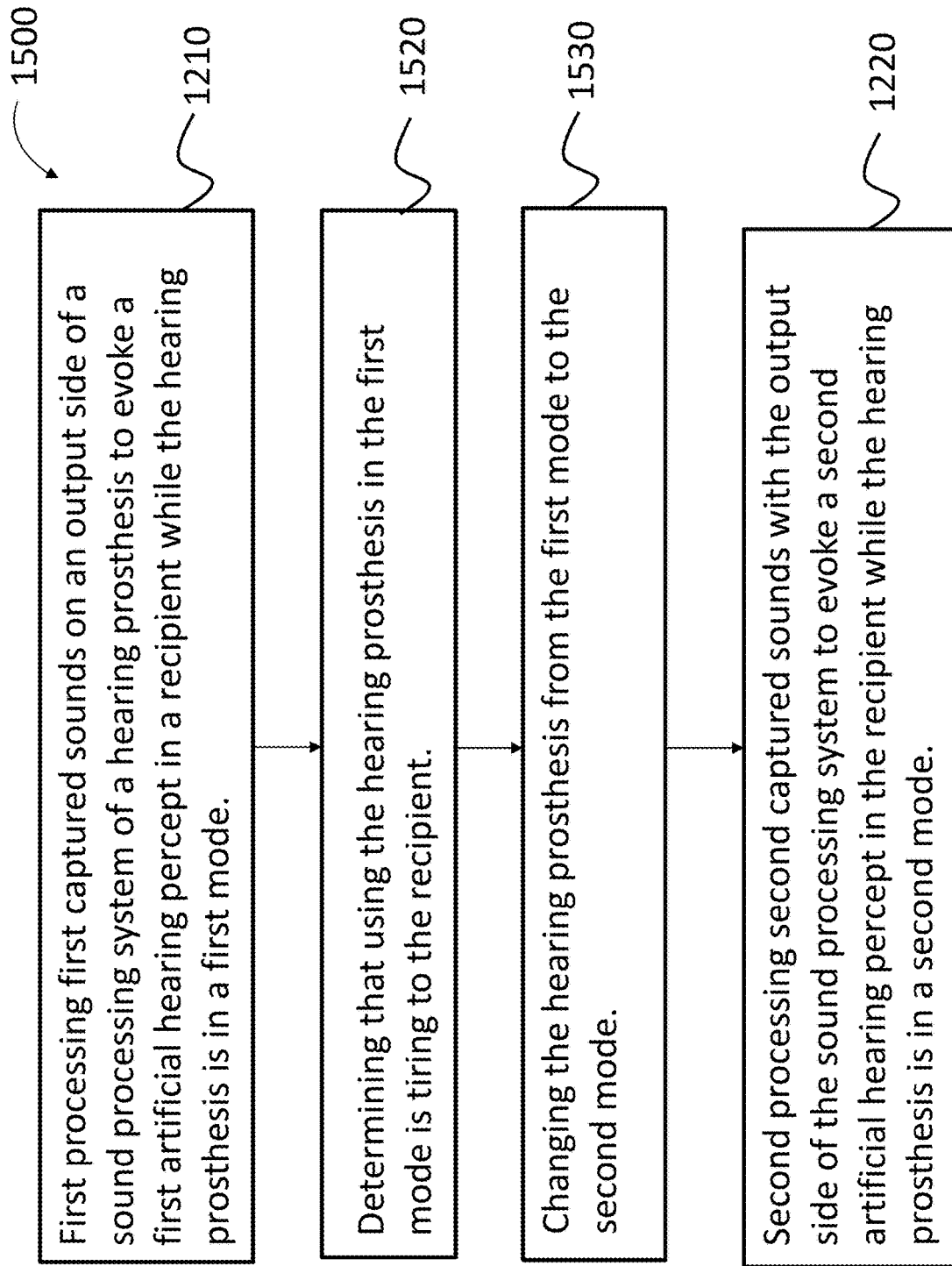
FIG. 15 presents another exemplary flowchart for an exemplary method according to an exemplary embodiment.

FIG. 15 depicts a flowchart for another exemplary method, method 1500. Method 1500 includes method action 1210, which corresponds to method action 1210 detailed above. Method 1500 further includes method action 1520, which entails determining that using the hearing prosthesis in the first mode is tiring. In an exemplary embodiment, this is executed by the recipient himself or herself. In an alternate exemplary embodiment, this can be determined by the hearing prosthesis itself, as will be explained in some additional detail below. Method 1500 further includes method action 1530, which entails changing the hearing prosthesis from the first mode to the second mode. As can be seen from FIG. 15, method 1500 further includes method action 1220, which corresponds to method action 1220 detailed above. It is to be understood that in an alternative embodiment, method 1500 can be expanded to repeat method actions 1520 and 1530 after method action 1220, albeit with respect to changing the prosthesis from the mode that it is currently into yet another mode, where this other mode is less tiring, or otherwise requires less effort to generally understand the captured sounds, all things being equal. It is to be understood that in further alternate embodiments, this concept can be further from more modes as the case will be.

A variety of reasons can prompt the recipient to implement method 1200, 1300, 1400, and/or 1500 (or any of the other methods detailed herein). In an exemplary embodiment, between method 1210 and method 1220, with respect to methods 1200 and 1500, an environmental change occurs that causes utilization of the hearing prosthesis in the first mode to be more tiring than that which was the case prior to the environmental change, all other things being equal. In this regard, by way of example only and not by way of limitation, the recipient can be exposed to an alcoholic beverage or otherwise the utilization of some form of drugs prescription or otherwise. Still further by way of example only and not by way of limitation, the recipient can be exposed to a more noisy environment and/or a speaker to which the recipient is listening is removed and another speaker who speaks less clearly has been presented in place of the former speaker. The recipient could simply be in a more distracting environment. It is noted that in an exemplary embodiment, the cognitive capabilities of the recipient between method action 1210 and method action 1220 remain the same. That said, in an alternative embodiment, the cognitive capabilities the recipient between method action 1210 and method action 1220 change such that the recipient has less cognitive capability with respect to method action 1220 than he or she did with respect to method action 1210. This is also the case with respect to fatigue. This concept is also applicable to methods 1300 and 1400 as well.

Figure 16:
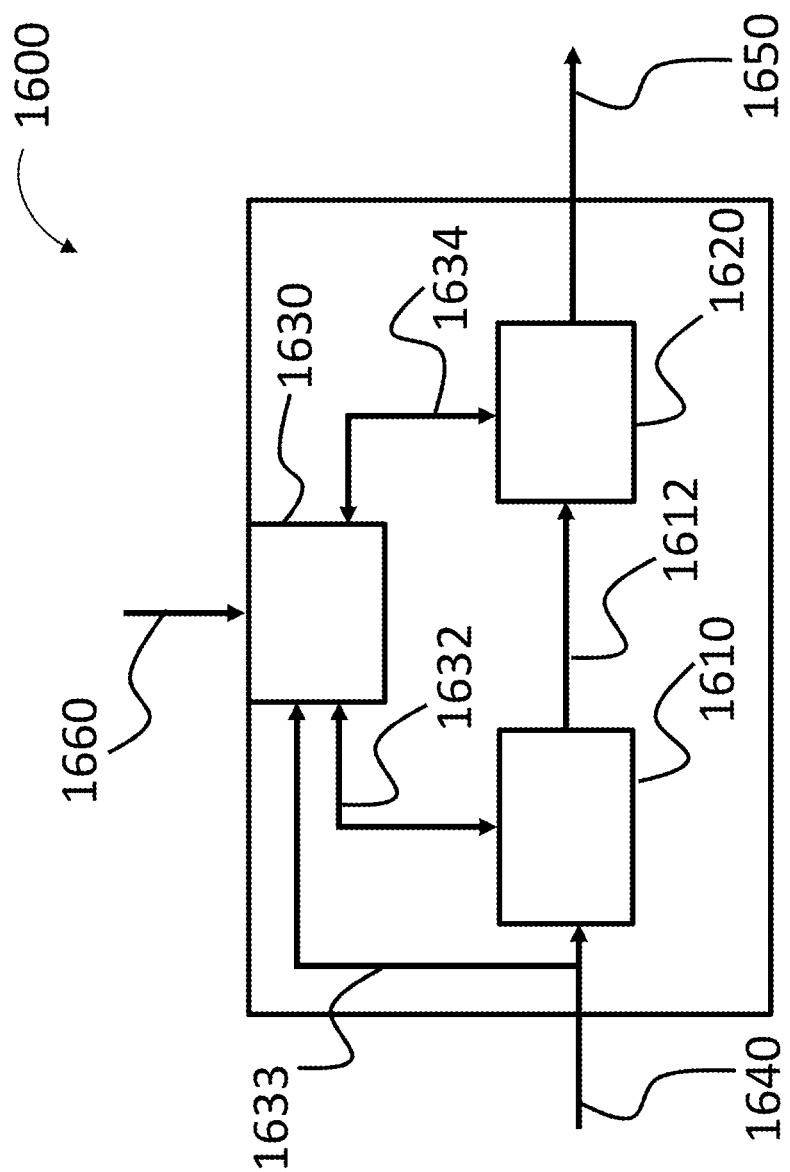
FIG. 16 presents an exemplary functional schematic according to an exemplary embodiment.

FIG. 16 presents a functional schematic of an exemplary prosthesis 1600, or at least a portion thereof, according to an exemplary embodiment. In an exemplary embodiment, the prosthesis 1600 corresponds to the retinal implant detailed above, while in other embodiments the prosthesis 1600 corresponds to the cochlear implant detailed above with respect to FIG. 1. That said, in some alternate embodiments, the prosthesis is another type of prosthesis, such as by way of example only and not by way of limitation, a middle ear implant or a bone conduction device implant. In an exemplary embodiment, the prosthesis 1600 includes a processor 1610, which in an exemplary embodiment, can be a light processor and/or a sound processor. The processor 1610 receives a signal 1640 indicative of input that is based upon a captured physical phenomenon, such as sound, light, etc. The processor 1610 processes the input 1640, and outputs a signal 1612 that is based on the processed input to tissue stimulator 1620. In an exemplary embodiment, tissue stimulator 1620 is configured to stimulate the tissue to evoke a hearing percept based on the signal 1612. This is represented by output arrow 1650, which represents the output of stimulative energy to tissue of the recipient. In an exemplary embodiment, the output is an electrical signal, such as the case with respect to the output of an electrode of a retinal implant and/or a cochlear implant.

Prosthesis 1600 further includes an input unit 1630, which is configured to receive input indicative of a dynamic cognitive capability of a recipient. In an exemplary embodiment, input unit entails a toggle switch or the like that is configured so that the recipient can depress the switch so as to provide input, represented by input 1660, into the input unit. The input unit 1630 is in signal communication with the processor 1610 via signal path 1632. In an exemplary embodiment, the input unit 1630 receives the input 1660 from the recipient that indicates that the recipient is of a certain dynamic cognitive capacity (more on this below). In an exemplary embodiment, the input unit 1630 receives the input 1660 from the recipient indicating that the recipient wants the prosthesis to operate differently from that which it is currently operating, because, for example, the cognitive capability of the recipient has changed and/or because the recipient has become fatigued and/or because the sound and/or light that the recipient is receiving requires more cognitive effort specifically or effort in general to comprehend, all other things being equal. That said, as will be detailed below, input unit 1630 further includes, in some embodiments, the capability to receive input indicative of latent variables or the like that are indicative of the recipient becoming fatigued, the recipient having less cognitive capability than that which was previously the case and/or that the sound and/or light to which the recipient is being exposed requires more effort to comprehend.

Briefly, still with reference to FIG. 16, it can be seen that the input unit 1630 is in communication with the sound processor 1610 via signal line 1632, which will enable the input unit 1630 to provide input to the sound processor so that the sound processor processes sounds in a different manner according to the teachings detailed herein, which corresponds to a different operating regime and/or different operating mode and/or operating the prosthesis differently. Also as can be seen from FIG. 16, the input unit 1630 is in communication with the tissue stimulator 1620 via signal line 1634. In an exemplary embodiment, input unit 1630 can communicate directly with the tissue stimulator 1620, and, in some embodiments, control the tissue stimulator 1620 so that the prosthesis 1600 operates differently. That is, the input unit 1630 bypasses the processor 1610 and the input unit 1630 in combination with the tissue stimulator 1620 changes the operating regimes of the prosthesis 1600. In an exemplary embodiment, this can entail the elimination of certain channels from being outputted by the tissue stimulator 1620. In an exemplary embodiment, this can entail the prevention of energizement of one or more electrodes of an electrode array where the tissue stimulator 1620 is a cochlear electrode array. It is noted that the input unit 1630 can work with both the processor 1610 and the tissue stimulator 1620 at the same time to achieve any of the results detailed herein and/or variations thereof.

Accordingly, in an exemplary embodiment, the prosthesis 1600 is configured to receive input indicative of a dynamic cognitive capacity of a recipient and/or input indicative of a dynamic fatigue state of the recipient. In an exemplary embodiment, as noted above, the recipient can depress a button on the prosthesis that is part of input unit 1630. In an exemplary embodiment, the prosthesis is configured such that the default is to operate in the third regime as detailed above. That is, upon commencement of the utilization of the prosthesis 1600, the prosthesis operates in the third regime unless input is inputted into the prosthesis. Subsequently, the recipient becomes fatigued to the first level and/or recognizes that he or she has experienced a cognitive capability declined relative to that which was the case at the commencement of utilization of the prosthesis 1600. Accordingly, the recipient can provide input into the input unit 1630, such as by depressing a button on the input unit, indicating such. Upon receipt of this input, the prosthesis is configured to transition from the third operating regime to the first operating regime. Subsequently, the recipient becomes fatigued to the second level and/or recognizes that he or she has experienced a cognitive capability decline relative to that which was the case at the time that the recipient previously inputted the information regarding the fatigue and/or cognitive capability declined just noted. Accordingly, the recipient can provide input into the input unit 1630, such as by depressing the button on the input unit, indicating such. The prosthesis is configured to recognize that the button has been depressed a second time, and therefore, upon such recognition, the prosthesis is configured to transition from the first operating regime to the second operating regime.

Note that additional operating regimes can be utilized after the second operating regime that entailed further downshifting of the various capabilities of the hearing prostheses with respect to the output side processing 300. Thus, as noted above, there could be a fourth operating regime in which the prosthesis operates that requires even less cognitive effort to generally comprehend the content of the input 1640. There could be additional operating regimes, each operating regime being or otherwise corresponding to a further downshifting of the prosthesis 1600. That said, in the embodiment where there are only three operating regimes, the prosthesis 1600 is configured such that the third time that the button of the input unit 1630 is depressed, the prosthesis reverts back to the third operating regime. In an exemplary embodiment, the prosthesis 1600 interprets the third depression of the button of the input unit 1630 as indicating that the recipient is at a zero fatigue level and/or at the maximum cognitive capability level and/or that the environment in which the recipient is in is such that the recipient requires relatively little effort to comprehend the input relative to that which was previously the case.

While the embodiments detailed above has been presented in a digital/discreet manner, in some alternate embodiments, the input 1630 can be utilized in more of an analog manner. In an exemplary embodiment, the recipient can turn a knob that gradually adjusts the prosthesis through different operating regimes, although even that has a modicum of digitality thereto. Note further that in an exemplary embodiment, the prosthesis 1600 can be configured such that the recipient can control one or more or all of the various output side processing features detailed above. By way of example only and not by way of limitation, in an exemplary embodiment, the recipient can adjust the number of spectral maxima on his or her or her own to the exact number that he or she finds acceptable. In an exemplary embodiment, the recipient could adjust the pulse rate to that which he or she finds acceptable. Any of the parameters that can be adjusted detailed herein can be individually adjusted in some embodiments.

It is noted that in at least some exemplary embodiments, the input required to adjust these specific features could become voluminous. In this regard, in an exemplary embodiment, the prosthesis 1600 can be configured to communicate with a portable handheld electronic device, such as by way of example, a so-called smart phone and/or a so-called laptop computer. Such devices can enable more ease of management and/or more ease of input of the various parameters that can be adjusted as detailed herein and/or other parameters that can be adjusted to account for fatigue and/or for varying cognitive capacity, and/or for input that requires more effort.

The term "downshifting" has been used herein to describe the changes to the operation of the hearing prosthesis. In this regard, the term "downshifting" is meant to mean that the prosthesis is operated in a manner such that the prosthesis operates in a less than optimal matter for conditions that would otherwise warrant the more optimized matter. In this regard, this differentiates from a scenario where, for example, a hearing prosthesis is changed from an Omni directional mode to a beamforming or directional capture mode because that scenario warrants such operation. Conversely, downshifting would entail utilizing beamforming or directional capture mode even though the situation would otherwise not call for such, solely because the recipient has become fatigued and/or the recipient has experienced reduced cognitive capability. It is noted that the term "downshifting" as used herein corresponds to short-term changes to address short-term fatigue and/or cognitive fluctuations. This in a manner analogous to utilizing a vehicle at a lower gear setting for a specific reason. A long-term change would be analogous to devoting a car or truck to utilization on a steep mountainside where, for example, the car or truck would always be operated in first gear.

Still further, the term downshifting as used herein is directly tied to the current state of the recipient whether that is an affirmative input by the recipient or a determination by the prosthesis based on latent variables or the like. To be clear, this differentiates from establishing or otherwise operating the prosthesis in a given operating regime because the recipient has that specific cognitive capability on a long-term basis and/or has a mental condition that warrants such in a manner analogous to fatigue (e.g., a very rich and successful hearing impaired person with knowledge or talent that people will stand in the cold rain for hours to acquire may not care if he or she does not pick up nuances of voice in a given operational regime because that operational regime "pains" the recipient—here, the recipient views utilizing the prosthesis at that operational regime as tiring or fatiguing, and just does not care if people have to repeat themselves 3 or 4 times—this as distinguished from someone who adjusts the operating regime because he or she has become tired at that limited temporal period or he or she is not as cognitively sharp as previously was the case).

Another way of qualifying some of the teachings detailed herein is that the recipient can adjust the operational regimes of the prosthesis to achieve an output thereof that is more manageable than other operational regimes. By analogy, one goat is easier to herd than two goats, two goats are easier to herd than three goats, three goats are easier to herd than for goats etc., all other things being equal. In the same vein, less information/less content in the output 1650 of the prosthesis is easier to manage than more content, all other things being equal.

The embodiments detailed above have focused on recipient input as a conscious act into input 1630. As noted above, in an alternate embodiment, the prosthesis can utilize latent variables to determine or otherwise indicate that the recipient is at a fatigue level and/or that the recipient has experienced a change in his or her dynamic cognitive capabilities and/or that a change has occurred in an environment that requires more effort to comprehend the given input relative to that which was the case, all other things being equal.

It is noted that in an exemplary embodiment, the prosthesis 1600 alone, and/or in combination with another external device, such as a smart phone and/or a laptop computer, is configured with software, and/or hardware, and/or firmware, or the like to "learn" from the recipient and extrapolate when the recipient is more likely to be fatigued and/or when the recipient is more likely to experience a diminished cognitive capability relative to other instances.

In an exemplary embodiment, the prosthesis is configured to record, on a temporal basis, the changes made to the operating regimes of the prosthesis. For example, a college student may become more fatigued during a 10:00 AM class than that which was the case at an 8:30 AM class. Over the course of a number of occurrences of the recipient changing the prosthesis from one operating regime to the other operating regime, the prosthesis can extrapolate a pattern, and therefore can configure itself to automatically adjust to the pertinent operating regime at the pertinent time without the recipient having to provide input to the recipient. Here, in an exemplary embodiment, the prosthesis can provide a signal to the recipient indicating that such has been performed, and the recipient can override such if he or she seeks to do so. In an alternate embodiment, the prosthesis provides no indication of the recipient, and the recipient can override such if he or she seeks to do so. Accordingly, in an exemplary embodiment, the prosthesis is configured to remember the prior "downshiftings" or the like, and can extrapolate a scheduled therefrom and implement such. Note further that in an exemplary embodiment, instead of automatically implementing such, the prosthesis can present the schedule to the recipient, and can ask the recipient to agree to the schedule and/or ask for modifications to the schedule. Such can be enabled via a portable handheld electronic device, or the like.

While the above embodiment has been detailed in terms of a reoccurring scenario that can be temporally correlated, other embodiments can utilize a reoccurring scenario that is correlated to other features, such as temperature, ambient noise, geography (e.g., a GPS can be utilized to determine location and/or correlation between, cell phone towers can be utilized to determine location—the prosthesis can "remember" the geographic locations where the recipient provided input to the prosthesis to downshift or the like, and develop a geographic schedule based therefrom, etc.). Still further, in an exemplary embodiment, the prosthesis can "learn" that downshifting occurs as a result of certain frequencies predominating an input to the prosthesis (e.g., speech frequencies, flesh colored frequencies, etc.). The prosthesis thus correlates the downshifting to the level of fatigue or the level of cognitive capability experienced by the recipient at the time of downshifting.

In an exemplary embodiment, the prosthesis 1600 can be configured to extrapolate a pattern based on a level and/or duration of ambient noise. In an exemplary embodiment, if the duration of ambient noise extends for certain temporal period, and the recipient frequently or otherwise statistically significantly changes or otherwise downshifts the prosthesis after the noise is extended to that temporal period, the prosthesis can be configured to extrapolate that pattern and then automatically downshift upon the occurrence of the noise for that temporal period. In an exemplary embodiment, the recipient might downshift two or more levels for a given period, or might downshift gradually with respect to the length of the noise. Any correlation between the length and/or volume of noise and the recipient's fatigue and/or cognitive capabilities that can enable the teachings detailed herein and/or variations thereof to be practiced can be utilized in at least some exemplary embodiments.

Still further, in an exemplary embodiment, the prosthesis can extrapolate fatigue level and/or cognitive capability from the speech of the recipient. In an exemplary embodiment, the rate of speech/words can be an indicator of fatigue and/or cognitive capability and/or the effort to which the recipient is placing towards listening or seeing. Still further, in an exemplary embodiment, the voice level can be an indicator of fatigue and/or cognitive capability and/or the effort to which the recipient is placing towards listening or seeing. With regard to the latter, in an exemplary embodiment, a voice stress analysis can be utilized, where increased stress indicates that more effort is being applied to listening or seeing. In an exemplary embodiment, the prosthesis can correlate input 1660 by the recipient into the input unit 1630 with these latent variables and can train itself to automatically downshift upon such occurrences.

As can be seen, in an exemplary embodiment, the training or the like is based on semi-random events that when collected together, can establish a pattern that can be utilized for automatic operational adjustment. That is, the events are dictated by the recipient's lifestyle, and the recipient's lifestyle is for the most part established because the recipient has the ability to artificially hear and/or artificially see. That is, the events are not associated with training or otherwise optimizing the hearing prosthesis, but instead are events that occur during normal life, which events occur while the recipient has different fatigue levels and/or no fatigue levels and/or has different cognitive capabilities, and in many instances, from one occurrence of the same event to another occurrence of the same event, and the operation of the hearing prosthesis is modified accordingly to accommodate the recipient's state during those events.

Note further that in some exemplary embodiments, fatigue can be determined utilizing body movements, and/or other physiological features, such as output from an accelerometer which analyzes the recipient's activity. Note further that with respect to FIG. 16, it is noted that the input into input unit 1630 not only includes input by the recipient via the pushbuttons detailed above or the like, but also includes input that is not initiated by the recipient, such as the input from the accelerometer just described. Note further that input into the input unit 1630 can flow from the capture device. By way of example, the microphone 210 can provide input into the input device 1630. The input device 1630 can also be a control unit or the like where a processor in and of itself processes this input and extrapolates data from the input (e.g., that the frequencies captured by the microphone are primarily voice frequencies, etc.) and utilizes that to develop the aforementioned automatic downshifting routines of the like. Accordingly, as can be seen in FIG. 16, the input 1640 is also fed to the input unit 1630 via signal line 1633. That said, input into the input unit 1630 can also be provided from the processor 1610 via signal line 1632. In this regard, the results of processing can be utilized by the input unit 1630 to ascertain or otherwise extrapolate a level of fatigue and/or level of cognitive capability and/or a level of effort associated with comprehending the information that is captured by the prostheses. In a similar vein, input unit 1630 is in communication with tissue stimulator 1620. The input unit 1630 can evaluate information from the tissue stimulator, and extrapolate a level of fatigue and/or a level of cognitive capability and/or a level of effort associated with comprehending the information that is captured by the prosthesis based on how the prosthesis is going to evoke a percept based on the information captured by the prosthesis.

Figure 17:
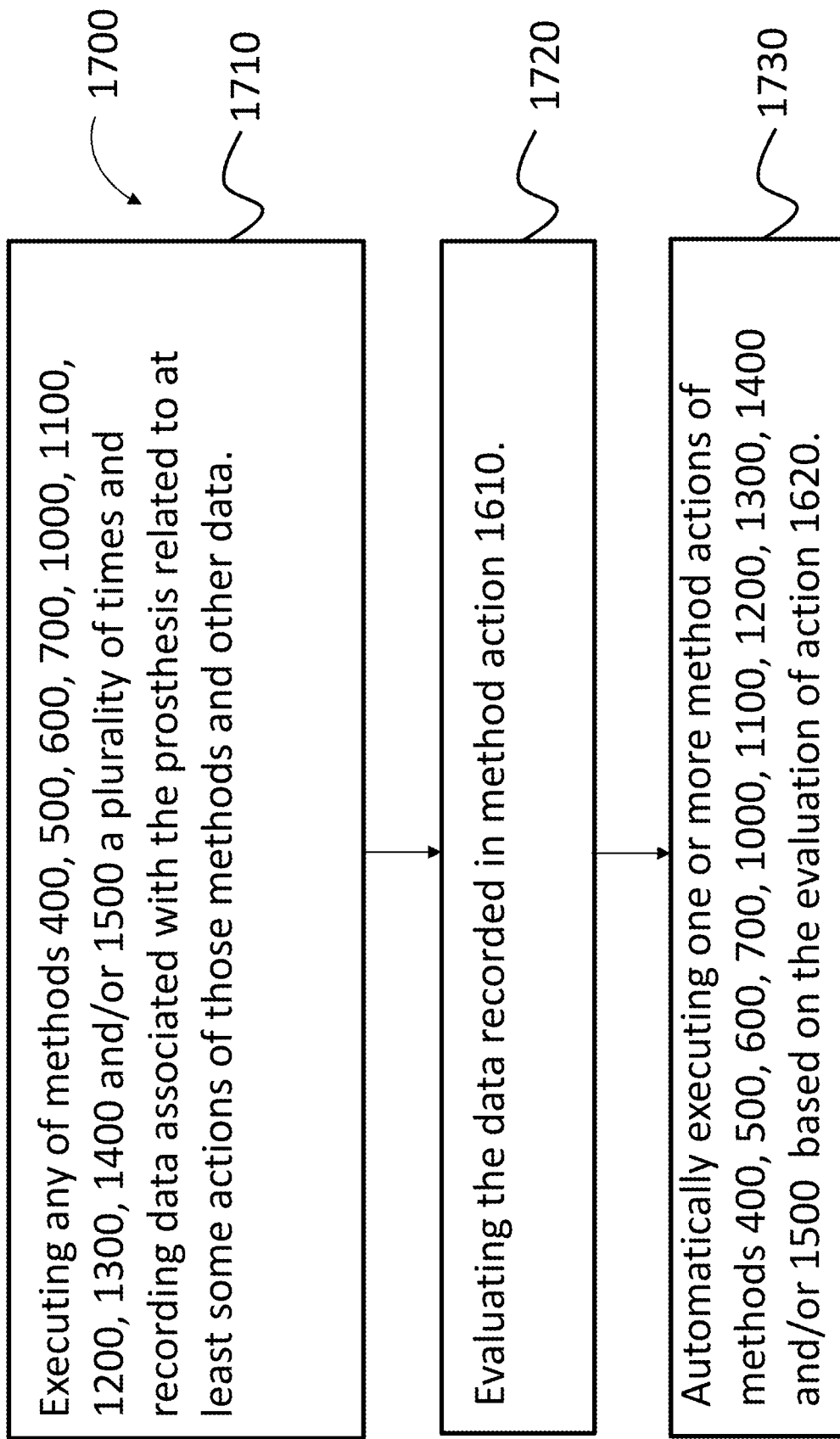
FIG. 17 presents another exemplary flowchart for an exemplary method according to an exemplary embodiment.

In view of the above, FIG. 17 presents an exemplary method 1700. Method 1600 includes method action 1610, which entails executing any of methods 400, 500, 600, 700, 1000, 1100, 1200, 1300, 1400, and/or 1500 (or any other method detailed herein or portion thereof) a plurality of times and recording data associated with the prosthesis related to at least some actions of those methods (e.g., the operating regime to which the prosthesis was changed, the stimulation rate to which the prosthesis was changed) and other data (e.g., time, date, geographic location, etc.). Method 1700 further includes method action 1720, which entails evaluating the data recorded in method action 1710. This can be done automatically by the thesis and/or by a remote electronic device. In an alternative embodiment, this can be performed by a third-party where the data recorded in action 1710 is provided to an off-site location where the data is evaluated. Accordingly, in at least some exemplary embodiments, method action 1620 can be substituted for the action of providing the data recorded in method action 1710 to a party so that it can be evaluated. Method 1700 further includes method action 1730, which entails automatically executing one or more the method actions of methods 400, 500, 600, 700, 1000, 1100, 1200, 1300, 1400, and/or 1500, or any other methods detailed herein or portions thereof based on the evaluation of action 1720. In an exemplary embodiment, between action 1720 and action 1630, there can be an action of programming or otherwise reconfiguring the prosthesis such that the one or more method actions of methods 400, 500, 600, 700, 1000, 1100, 1200, 1300, 1400, and/or 1500, or any other methods detailed herein or portions thereof are executed automatically. Accordingly, there exists a prosthesis that is programmed or otherwise configured so as to execute method 1730 automatically.

In view of the above, it can be understood that in an exemplary embodiment, the teachings detailed herein and/or variations thereof can have utilitarian value with respect to enabling a recipient to meet a subjective minimum level of information acquisition an understanding while preventing any additional unnecessary effort associated with listening and/or seeing. That is, in an exemplary embodiment, the prosthesis is configured so as to varyingly provide the "minimum" information that a recipient desires without more.

Note further that the converse is the case in some exemplary embodiments. In an exemplary embodiment, the hearing prosthesis is configured to enable the recipient to upshift so as to obtain more than a subjective minimum. Accordingly, exemplary embodiments include methods where after the downshifting there is a subsequent upshifting, either to the ultimate upshift operating regime (e.g., the third operating regime detailed above where the prosthesis is operating at maximum utility), or to an operating regime that provides the ability to extract more from that evoked hearing percept but not the maximum utility. Corollary to this is that some embodiments include methods where the cognitive capability of the recipient increases and/or the recipient becomes less fatigued, hence the upshifting.

As detailed above, there is utilitarian value in modifying the output side processing based on fatigue and/or cognitive load and/or the effort associated with comprehending or otherwise listening and/or viewing, utilizing the various prostheses detailed herein. Corollary to this is that in an exemplary embodiment, there is utilitarian value in applying such strategies to the ultimate output of a given prosthesis on a systematic level. Now with respect to a hearing prosthesis, FIG. 1800 functionally represents a bimodal and a hybrid hearing prosthesis (the two are different, but for the purposes of this disclosure, the diagram of FIG. 18 can be utilized to convey the pertinent teachings associated with both systems). In this exemplary embodiment, input 1810 is provided to a main component 1820 of the prosthesis, which main component is in signal communication with tissue stimulator subsystem 1830 and tissue stimulator subsystem 1840 as can be seen. In an exemplary embodiment, tissue stimulator subsystem 1830 includes a separate tissue stimulator than that of tissue stimulator subsystem 1840. In an exemplary embodiment, subsystem 1830 corresponds to a first cochlear implant electrode array and associated stimulator unit, and subsystem 1840 corresponds to a second cochlear implant electrode array and associated stimulator unit. Each subsystem is utilized for the respective ear of the recipient. In another exemplary embodiment, subsystem 1830 corresponds to a first type of hearing prosthesis, such as by way of example only and not by way of limitation, a cochlear implant, a middle ear implant, an inner ear mechanical stimulator, a bone conduction device, or a conventional acoustic hearing aid. In this exemplary embodiment, subsystem 1840 corresponds to a second type of hearing prosthesis different than that of the subsystem 1830 in an exemplary embodiment, for purposes of discussion, the first subsystem 1830 is a conventional acoustic hearing aid, and the second subsystem 1840 is a cochlear implant. In some embodiments, the subsystems are utilized in the same ear (e.g., there is residual hearing in an ear in which the cochlear election array is implanted).

Main component 1820 receives an input signal 1810 in a traditional manner (e.g., utilizing a microphone or plurality of microphones, etc.) and processes that input signal so that the various subsystems 1830 and 1840 can operate accordingly. In an exemplary embodiments utilizing the acoustic hearing aid in combination with a cochlear implant, low-frequency sound will be directed to the acoustic hearing aid 1830 (or more accurately, main component 1820 will divide up the input signal 1810 so as to output a signal to the acoustic hearing aid to evoke a hearing percept at those lower frequencies), and high-frequency sound will be directed to the cochlear implant 1840 (or more accurately, main component 1820 will divide up the input signal 1810 so as to output a signal to the cochlear implant to evoke a hearing percept at those higher frequencies). It is noted that the main component 1820 can include a sound processor configured to develop control signals for both subsystems 1830 and 1840. That said, in an alternate embodiment, main component 1820 is bifurcated between two components that operate independently of one another. Any arrangement that will enable the practice of a hybrid and/or a bimodal hearing prosthesis can be utilized in at least some exemplary embodiments.

In an exemplary embodiment, in a scenario where the recipient is at one or more of the fatigue levels detailed herein and/or in a scenario where the recipient is at a cognitive level of reduced capacity relative to that of other levels, and/or in a scenario where more effort is required to comprehend the input 1810, the subsystem 1840 can be shut down or otherwise disabled. In such an exemplary embodiment, this could mean that no high-frequency hearing percepts will be evoked by the prosthesis 1800. In an alternative embodiment, subsystem 1840 can operate in a reduced mode, where the intensity of the output of the subsystem is reduced (e.g., gain adjustments can be made to the subsystem 1840). It is noted that this can be done across the board for subsystem 1840, or, the more targeted features detailed above can be implemented with respect to subsystem 1840 (for example, the number of spectral maximas may be reduced, the stimulation rate can be reduced, etc.).

In an alternate embodiment, subsystem 1830 can operate in the reduced mode.

Figure 18:
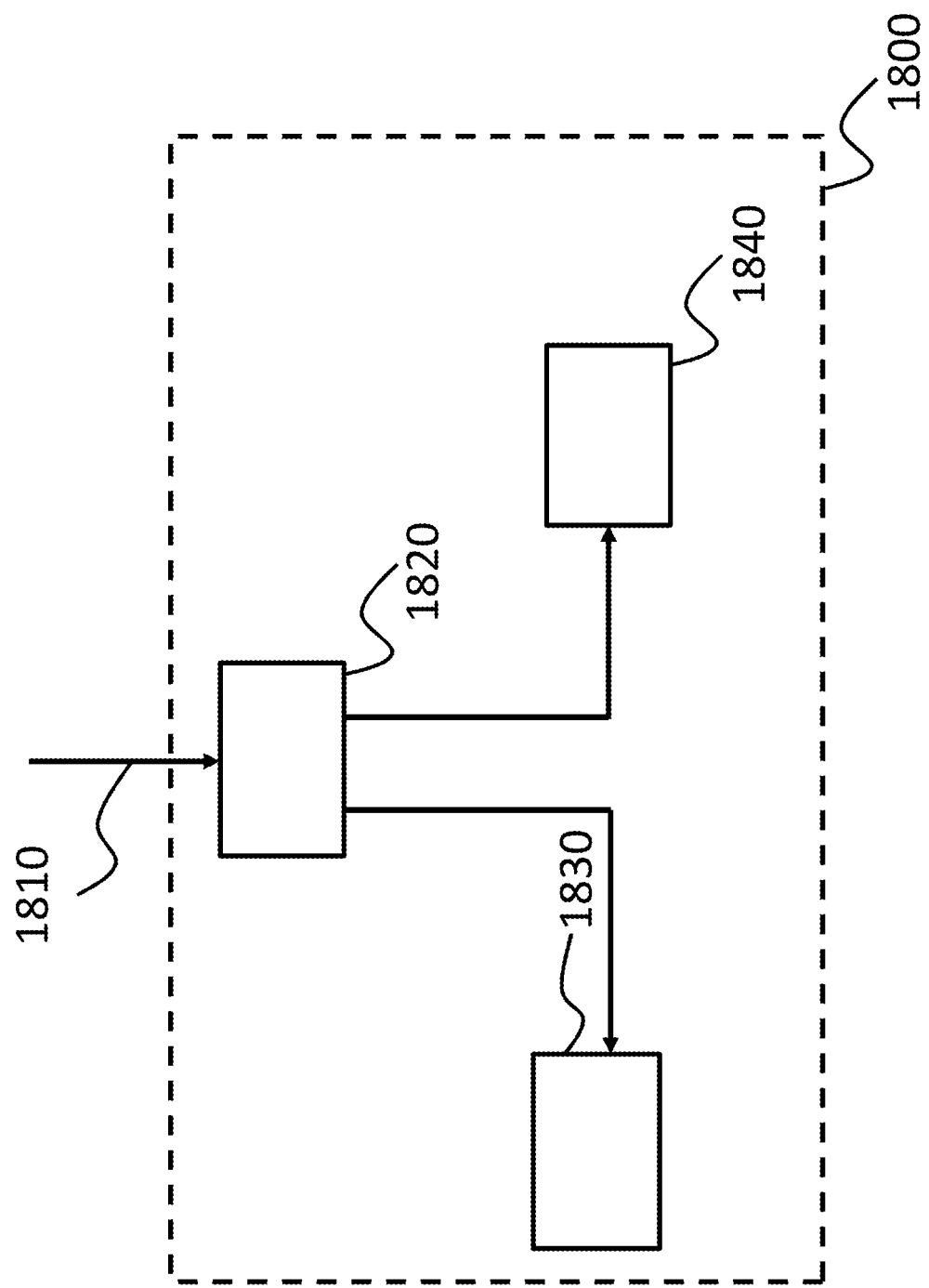
FIG. 18 presents an exemplary functional schematic according to an exemplary embodiment.

Still further, in an exemplary embodiment, one or more subsystems (it is noted that while the embodiment of FIG. 18 depicts two subsystems, more than two subsystems can be included in some exemplary embodiments) can be operated in a reduced mode (which includes being shut down completely). In an exemplary embodiment, a recipient may have better hearing in one ear versus the other. In an exemplary embodiment, the subsystem(s) evoking hearing percepts for the inferior ear might be operated in a reduced mode so that the recipient does not put effort (or at least significant effort) into hearing with that ear or otherwise puts less effort into hearing with that ear than is otherwise the case.

Indeed, in an exemplary embodiment, one or more of the subsystems can operate in a mode that evokes a hearing percept that is configured to relax the recipient or otherwise render the recipient less fatigued, where one or more of the other subsystems operate in the mode that provides information to the recipient and evokes a hearing percept to accomplish such. Still further, in an exemplary embodiment, the subsystem can operate in a mode that does not evoke a conscious hearing percept, but stimulates the nerves in a manner that is relaxing to the recipient's nervous system. Any manner of operating one subsystem differently than the other subsystem in a manner differently than that which would otherwise be the case, all things being equal, as a result of the recipients fatigue level and/or the absence thereof and/or the recipients cognitive capability or a change thereof or otherwise due to the effort associated with listening can be utilized in at least some exemplary embodiments.

It is noted that in an exemplary embodiment, where frequencies or other content are bifurcated between the two subsystems or trifurcated between three subsystems, etc., there can be utilitarian value with respect to folding back the content that would otherwise be present in a given subsystem into one of the other subsystems. By way of example only and not by way of limitation, a recipient may find the content of the cochlear implant to be easier to comprehend, but not as "fulfilling" as the content of a middle ear stimulator. In an exemplary embodiment, the middle ear stimulator can be shut down and all of the content can be supplied to the cochlear implant. In an exemplary embodiment, the recipient may find that the cochlear implant is harder to listen to or otherwise takes more effort than the acoustic hearing aid, even though the recipient has little to no residual high-frequency hearing. In an exemplary embodiment, the prosthesis 1800 shuts down the cochlear implant, and provides the content that would otherwise be provided by the cochlear implant to the acoustic hearing aid, albeit at a lower frequency of which the recipient can hear (i.e., a frequency corresponding to the residual hearing of the recipient).

It is noted that while the teachings detailed above have typically been directed towards the "output side processing" of the hearing prosthesis, some embodiments can be directed towards management of the input side processing and/or management of the pre-input side processing with respect to hybrid and/or bimodal prostheses. For example, one of the subsystems can be implemented using input that is different from another of the subsystems. In an exemplary embodiment, the cochlear implant subsystem can utilize directional sound capture and/or beamforming, while the acoustic hearing aid subsystem can utilize omnidirectional sound capturing. Such can be done, for example, in a scenario where the recipient finds the acoustic hearing aid easier or less effortful to utilize. That said, in a scenario where the recipient finds the cochlear implant to be easier or less effortful to utilize, the omnidirectional sound capture can be utilized therefore, and the beamforming/directionality sound capture can be used for the acoustic hearing aid.

Some exemplary input side processing that can be different includes noise cancellation and/or feedback cancellation routines. In an exemplary embodiment, the operating regimes of the prosthesis can correspond to utilizing different such routines depending on the level of fatigue or lack thereof of the recipient and/or depending on the cognitive ability of the recipient and/or depending on how much effort is associated with comprehending the evoked hearing percepts. By way of example only and not by way of limitation, adaptive signal processing associated with noise cancellation, including body noise cancellation, can be varied between the subsystems. For example, the attack time of an adaptive system can be varied depending on the fatigue and/or cognitive capabilities of the recipient, etc.

It is noted that any method detailed herein also corresponds to a disclosure of a device and/or system configured to execute one, or more, or all of the method actions associated therewith detailed herein. In an exemplary embodiment, this device and/or system is configured to execute one, or more, or all of the method actions in an automated fashion. That said, in an alternate embodiment, the device and/or system is configured to execute one, or more, or all of the method actions after being prompted by the recipient.

It is noted that embodiments include non-transitory computer-readable media having recorded thereon a computer program for executing one or more or any of the method actions detailed herein. Indeed, in an exemplary embodiment, there is a non-transitory computer-readable media having recorded thereon, a computer program for executing at least a portion of at least one of the methods detailed herein/one or more or all method actions detailed herein.

It is further noted that any device and/or system detailed herein also corresponds to a disclosure of a method of operating that device and/or using that device. Furthermore, any device and/or system detailed herein also corresponds to a disclosure of manufacturing or otherwise providing that device and/or system.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A method, comprising:
operating a bone conduction hearing prosthesis, wherein the action of operating includes operating the prosthesis at a given output level;
adjusting the output level of the bone conduction device based on a changed cognitive capacity of the recipient; and
operating the bone conduction hearing prosthesis at the adjusted output level.

2. The method of claim 1, wherein:
the method includes automatically adjusting the output level of the bone conduction device based on the changed cognitive capacity.

3. The method of claim 1, wherein:
the action of adjusting the output level of the bone conduction device based on cognitive capacity includes reducing compression for an increase in cognitive capacity.

4. The method of claim 1, wherein:
the output level is an amount of stimulation provided to the recipient.

5. The method of claim 1, wherein:
the hearing prosthesis is part of a system configured to receive input indicative of a cognitive capacity of the recipient;
the system adjusts operation of the prosthesis based on the input so that the output level has a higher amount of noise relative to that which would be the case with a fully implemented noise cancelation system of the prosthesis, even though the recipient has a reduced cognitive capacity;
the method includes receiving input indicative of the cogitative capacity by the system; and
the action of adjusting the output level results in the higher amount of noise.

6. The method of claim 1, further comprising:
obtaining data indicative of cognitive capacity of the recipient; and
evaluating the obtained data remotely from the hearing prosthesis, wherein
the action of adjusting the output level of the bone conduction device based on the changed cognitive capacity of the recipient is based on results of the action of evaluating.

7. The method of claim 1, further comprising:
receiving data on a portable electronic device including recipient input adjustments and correlating the received data with passively collected data and developing a basis to control the adjustment of the output level based on the correlated data, wherein
the action of adjusting the output level of the bone conduction device based on the changed cognitive capacity of the recipient is based on the developed basis.

8. The method of claim 1, wherein:
the action of adjusting the output level of the bone conduction device based on cognitive capacity includes increasing compression for a decrease in cognitive capacity.

9. A method, comprising:
capturing sound with a transducer;
obtaining data indicative of latent variables having a *nexus* with a recipient of a hearing prosthesis being fatigued; and
evoking a hearing percept using the hearing prosthesis based on the captured sound, wherein
the evoked hearing percept is evoked based on processing output of the transducer in a manner that takes into account the obtained data, thereby influencing the evoked hearing percept in such a manner that affirmatively takes into account recipient fatigue, and the method is automatically executed using a system that is trained to recognize the latent variables and automatically adjust the processing based on the recognition.

10. The method of claim 9, wherein:
the latent variable is associated with a geographic location.

11. The method of claim 9, wherein:
the manner that takes into account the obtained data changes a Q factor of the hearing prosthesis.

12. A hearing prosthesis comprising:
a sound processor; and
a sound capture device, wherein
the hearing prosthesis is configured to provide a signal based on sound captured by the sound capture device to the sound processor and configured to provide output to a recipient of the hearing prosthesis based on output from the sound processor that is based on the signal to evoke a hearing percept in the recipient via the output provided to the recipient,
the hearing prosthesis is configured to adjust the output based on cognitive capacity of the recipient, and
the hearing prosthesis is a bone conduction device.

13. The hearing prosthesis of claim 12, wherein:
the hearing prosthesis is configured to adjust gain of the hearing prosthesis based on cognitive capacity of the recipient to adjust the output based on cognitive capacity of the recipient.

14. The hearing prosthesis of claim 12, wherein:
the hearing prosthesis is configured to adjust magnitudes/amplitudes of some frequencies of the output so that they are higher relative to other frequencies beyond that which would otherwise be the case so as to adjust the output based on cognitive capacity.

15. The hearing prosthesis of claim 12, wherein:
the hearing prosthesis is configured to communicate with a portable electronic device configured to receive data relevant to cognitive capacity of the recipient, and
the adjustment of the output based on cognitive capacity is based on the data received by the portable electronics device.

16. The hearing prosthesis of claim 15, wherein:
the portable electronic device is configured to manage at least some of a set of various parameters that can be adjusted to account for fatigue and/or varying cognitive capacity; and
the adjustment of the output based on cognitive capacity is based on the managed at least some of the set of various parameters that can be adjusted to account for fatigue and/or varying cognitive capacity.

17. The hearing prosthesis of claim 15, wherein:
the portable electronic device is configured to receive user input adjustments; and
the hearing prosthesis is configured to adjust the output based on the received user input adjustments.

18. The hearing prosthesis of claim 12, wherein:
the adjusted output is an adjustment of the intensity of the output that evokes a hearing percept.

19. The hearing prosthesis of claim 12, wherein:
the hearing prosthesis is configured to automatically adjust the output based on cognitive capacity of the recipient, and
the hearing prosthesis is configured to enable the recipient to specifically override the adjustment.

20. The hearing prosthesis of claim 12, wherein:
the hearing prosthesis is part of a system that includes a mobile phone, wherein the mobile phone is configured to receive input indicative of recipient cognitive capacity, and
the system is configured to use the input indicative of recipient cognitive capacity to adjust the output based on cognitive capacity of the recipient.

21. The hearing prosthesis of claim 12, wherein:
the hearing prosthesis is configured to automatically extrapolate a cognitive capacity of the recipient based on the occurrence of a recurring scenario that has a correlation with reduced cognitive load of the recipient.

22. The hearing prosthesis of claim 12, wherein:
the hearing prosthesis is configured to, based on cognitive capacity, implement adaptive dynamic range optimization to focus processing on sound intensities that have a higher probability of being associated with sound that is deemed to be desired, thereby adjusting the output based on cognitive capacity of the recipient.

23. The hearing prosthesis of claim 12, wherein:
the hearing prosthesis is configured to communicate with a portable electronic device configured to receive data relevant to cognitive capacity of the recipient; and
at least one of the hearing prosthesis or the portable electronic device is configured with software, and/or hardware, and/or firmware that learns from the recipient and extrapolates when the recipient is more likely to be fatigued and/or when the recipient is more likely to experience a diminished cognitive capability relative to other instances; and
the cognitive capacity is based on the extrapolation.

24. A non-transitory computer-readable media having recorded thereon a computer program for executing the following actions:
automatically adjusting an output level of a bone conduction hearing prosthesis based on a fatigue level of a recipient of the prosthesis.

25. The media of claim 24, wherein:
the computer program is for further executing an action of stimulation reduction based on fatigue level, thereby automatically adjusting the output level.

26. The media of claim 24, wherein:
the computer program is for further executing an action of extrapolating fatigue level from speech of the recipient via a voice stress analysis thereof.

27. The media of claim 24, wherein:
the computer program is for further executing an action of analyzing output from a movement sensor and deducing fatigue level of the recipient therefrom.

28. The media of claim 24, wherein:
the computer program is for further executing an action of processing a signal based on captured sound by limiting a number of spectral maxima presented to the recipient in output of the prosthesis if the fatigue level indicates the recipient is fatigued relative to that which would otherwise be the case, thereby automatically adjusting the output level.

29. The media of claim 24, wherein:
the computer program is for further automatically executing an action of adjusting the output level based on identified recurring scenarios that have a correlation with the fatigue level of the recipient.

30. The media of claim 24, wherein:
the computer program is for further executing an action of extrapolating fatigue level from movement of the recipient via data from a motion detector.

* * * * *